(12) United States Patent
Yokoyama et al.

(10) Patent No.: US 9,005,776 B2
(45) Date of Patent: Apr. 14, 2015

(54) COMPOUND HAVING BENZOTRIAZOLE RING STRUCTURE AND ORGANIC ELECTROLUMINESCENT ELEMENT

(75) Inventors: Norimasa Yokoyama, Tsukuba (JP); Shuichi Hayashi, Tsukuba (JP); Naoaki Kabasawa, Tsukuba (JP); Yoshio Taniguchi, Ueda (JP); Musubu Ichikawa, Ueda (JP); Shunji Mochiduki, Shunan (JP)

(73) Assignees: Hodogaya Chemical Co., Ltd., Tokyo (JP); Shinshu University, Matsumoto-shi (JP)

( * ) Notice: Subject to any disclaimer, the term of this patent is extended or adjusted under 35 U.S.C. 154(b) by 465 days.

(21) Appl. No.: 13/257,142

(22) PCT Filed: Mar. 17, 2010

(86) PCT No.: PCT/JP2010/054603
§ 371 (c)(1),
(2), (4) Date: Sep. 16, 2011

(87) PCT Pub. No.: WO2010/107074
PCT Pub. Date: Sep. 23, 2010

(65) Prior Publication Data
US 2012/0012831 A1    Jan. 19, 2012

(30) Foreign Application Priority Data
Mar. 18, 2009  (JP) .................. 2009-065467

(51) Int. Cl.
| | | |
|---|---|---|
| H01L 51/54 | (2006.01) |
| C07D 401/14 | (2006.01) |
| C07D 401/04 | (2006.01) |
| C07D 401/10 | (2006.01) |
| C09K 11/06 | (2006.01) |
| H01L 51/00 | (2006.01) |
| H01L 51/50 | (2006.01) |
| H05B 33/10 | (2006.01) |
| H05B 33/14 | (2006.01) |

(52) U.S. Cl.
CPC ............ *C07D 401/14* (2013.01); *C07D 401/04* (2013.01); *C07D 401/10* (2013.01); *C09K 11/06* (2013.01); *C09K 2211/1007* (2013.01); *C09K 2211/1011* (2013.01); *C09K 2211/1029* (2013.01); *C09K 2211/1059* (2013.01); *H01L 51/0072* (2013.01); *H01L 51/5048* (2013.01); *H01L 51/5096* (2013.01); *H05B 33/10* (2013.01); *H05B 33/14* (2013.01)

(58) Field of Classification Search
None
See application file for complete search history.

(56) References Cited

U.S. PATENT DOCUMENTS

| | | |
|---|---|---|
| 6,387,992 B1 | 5/2002 | Pastor et al. |
| 2007/0003783 A1 | 1/2007 | Morishita et al. |
| 2008/0027226 A1* | 1/2008 | Rogers et al. ................ 546/199 |

FOREIGN PATENT DOCUMENTS

| | | |
|---|---|---|
| JP | 8 48656 | 2/1996 |
| JP | 2734341 | 3/1998 |
| JP | 3194657 | 6/2001 |
| JP | 2004 520284 | 7/2004 |
| JP | 2006-264166 | 10/2006 |
| JP | 2007 518705 | 7/2007 |
| WO | 2004 092246 | 10/2004 |

OTHER PUBLICATIONS

Lipke, B., et al., "Zur Kenntnis von N-(Phenyl)-pyridiniumsalzen;[1]) Reaktivitat des N-(3-Nitro-4-chlorphenyl)-pyridiniumchlorids," Z. Chem, vol. 12, No. 3, pp. 103-104, (1972).

Hosokawa, C., et al., Japan Society of Applied Physics Ninth Workshop Preprint, pp. 55-61, (2001).

Wakimoto, T., "Optimization of driving lifetime durability in organic LED devices using phosphorescent guest emitter," Japan Society of Applied Physics Ninth Workshop Preprint, pp. 23-31, (2001).

"Organic LEDs using Hexaphenylbenzene Derivatives," Fiftieth Meeting of Japan Society of Applied Physics and Related Societies, Lecture Preprint, 28p-A-6, p. 1413, (Mar. 2003).

← 8 Cathode
← 7 Electron injection layer
← 6 Electron transport layer
← 5 Hole blocking layer
← 4 Luminescent layer
← 3 Hole transport layer
← 2 Transparent anode
← 1 Glass substrate Japan Society of Applied Physics, Journal of Organic Molecules/Bioelectronics Section (M&BE), vol. 11, No. 1, pp. 13-19, (2000).
International Search Report issued Apr. 20, 2010 in PCT/JP10/054603 filed Mar. 17, 2010.
Extended European Search Report issued Jul. 24, 2012, in Application No. 10753565.0-2117 / 2409974 PCT/JP2010054603.

* cited by examiner

*Primary Examiner* — J. L. Yang
(74) *Attorney, Agent, or Firm* — Oblon, McClelland, Maier & Neustadt, L.L.P.

(57) ABSTRACT

A compound having a benzotriazole ring structure and a formula (1):

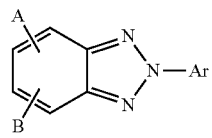

(1)

wherein Ar is a substituted or unsubstituted aromatic hydrocarbon group, aromatic heterocyclic group, or condensed polycyclic aromatic group; A and B are the same as or different from each other and each represent a hydrogen atom or a monovalent group of formula (2), provided that A and B are not simultaneously hydrogen atoms:

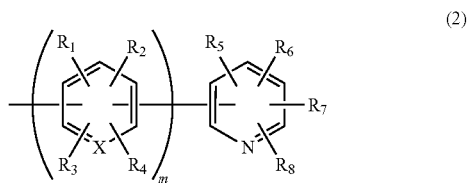

(2)

wherein $R_1$ to $R_8$ are the same as or different and each represent a hydrogen atom, a deuterium atom, a fluorine atom, a chlorine atom, a cyano group, a trifluoromethyl group, a linear or branched alkyl group having 1 to 6 carbon atoms, aromatic hydrocarbon group, a substituted or unsubstituted aromatic heterocyclic group, or condensed polycyclic aromatic group; m is an integer of 0, 1 or 2; X represents a carbon atom or a nitrogen atom; when X is a nitrogen atom, the nitrogen atom does not have substituents or bonding groups of $R_1$, $R_2$, $R_3$ and $R_4$; and when m is 2, a plurality of $R_1$, $R_2$, $R_3$, $R_4$ and X each are the same or different.

15 Claims, 2 Drawing Sheets

COMPOUND HAVING BENZOTRIAZOLE RING STRUCTURE AND ORGANIC ELECTROLUMINESCENT ELEMENT

TECHNICAL FIELD

The present invention relates to a compound suitable for an organic electroluminescence device which is a self-luminescent device suitable for various displaying devices and a device. More specifically, it relates to a compound having a benzotriazole ring structure and a pyridine ring structure, and to an organic electroluminescence device using the compound.

BACKGROUND ART

Since organic electroluminescence devices are self-luminescent devices, they are bright and excellent in visibility as compared with liquid-crystalline devices and capable of giving clear display, so that the organic electroluminescence devices have been actively studied.

In 1987, C. W. Tang et al. of Eastman Kodak Company put an organic electroluminescence device using organic materials into practical use by developing a device having a multi-layered structure wherein various roles are assigned to respective materials. In particular, they formed a lamination of a fluorescent material capable of transporting electrons and an organic material capable of transporting holes, so that both charges are injected into the layer of the fluorescent material to emit light, thereby achieving a high luminance of 1000 $cd/m^2$ or more at a voltage of 10 V or lower (see e.g., Patent Documents 1 and 2).

To date, many improvements have been performed for practical utilization of the organic electroluminescence devices, and high efficiency and durability have been achieved by an electroluminescence device wherein an anode, a hole-injection layer, a hole-transport layer, a light-emitting layer, an electron-transport layer, an electron-injection layer, and a cathode are sequentially provided on a substrate, to further segmentalize various roles (see e.g., Non-Patent Document 1).

Moreover, for the purpose of further improvement of luminous efficiency, utilization of triplet exciton has been attempted and utilization of a phosphorescent material has been investigated (see e.g., Non-Patent Document 2).

The light-emitting layer can be also prepared by doping a charge-transport compound, generally called a host material, with a fluorescent material or a phosphorescent material. As described in the above-mentioned Non-Patent Documents 1 and 2, the choice of the organic materials in organic electroluminescence devices remarkably affects various properties such as efficiency and durability of the devices.

In the organic electroluminescence devices, the charges injected from the both electrode are recombined in the light-emitting layer to attain light emission. However, since the mobility of holes is higher than the mobility of electrons, a problem of reduction in efficiency caused by a part of the holes passing through the light-emitting layer arises. Therefore, it is required to develop an electron-transport material in which the mobility of electrons is high.

A representative light-emitting material, tris(8-hydroxyquinoline)aluminum (hereinafter referred to as $Alq_3$) is commonly used also as an electron-transport material. However, since it has a work function of 5.8 eV, it cannot be considered that the material has hole-blocking capability.

As a technique to prevent the passing of a part of holes through the light-emitting layer and to improve probability of charge recombination in the light-emitting layer, there is a method of inserting a hole-blocking layer. As hole-blocking materials, there have been hitherto proposed triazole derivatives (see e.g., Patent Document 3), bathocuproine (hereinafter referred to as BCP), a mixed ligand complex of aluminum (BAlq) (see e.g., Non-Patent Document 2), and the like.

On the other hand, as an electron-transport material excellent in hole-blocking ability, there is proposed 3-(4-biphenylyl)-4-phenyl-5-(4-t-butylphenyl)-1,2,4-triazole (hereinafter referred to as TAZ) (see e.g., Patent Document 3).

Since TAZ has a work function as large as 6.6 eV and thus exhibits a high hole-blocking ability, it is used as an electron-transport hole-blocking layer to be laminated onto the cathode side of a fluorescence-emitting layer or phosphorescence-emitting layer prepared by vacuum deposition, coating or the like, and contributes to increase the efficiency of organic electroluminescence devices (see e.g., Non-Patent Document 3).

However, TAZ has a great problem of having low electron-transport property, and it is necessary to prepare an organic electroluminescence device in combination with an electron-transport material having a higher electron-transport property (see e.g., Non-Patent Document 4).

Further, BCP has a work function as large as 6.7 eV and a high hole-blocking ability, but has a low glass transition point (Tg) which is 83° C., so that it is poor in thin-film stability and thus it cannot be considered that it sufficiently functions as a hole-blocking layer.

All the materials are insufficient in thin-film stability or are insufficient in the function of blocking holes. In order to improve characteristic properties of the organic electroluminescence devices, it is desired to develop an organic compound which is excellent in electron-injection/transport performances and hole-blocking ability and is highly stable in a thin-film state.

PRIOR ART DOCUMENTS

Patent Documents

Patent Document 1: JP-A-8-48656
Patent Document 2: Japanese Patent No. 3194657
Patent Document 3: Japanese Patent No. 2734341

Non-Patent Document

Non-Patent Document 1: Japan Society of Applied Physics Ninth Workshop Preprint, pp. 55-61 (2001)
Non-Patent Document 2: Japan Society of Applied Physics Ninth Workshop Preprint, pp. 23-31 (2001)
Non-Patent Document 3: Fiftieth Meeting of Japan Society of Applied Physics and Related Societies, 28p-A-6 Lecture Preprint, p. 1413 (2003)
Non-Patent Document 4: Japan Society of Applied Physics, Journal of Organic Molecules/Bioelectronics Section, Vol. 11, No. 1, pp. 13-19 (2000)
Non-Patent Document 5: Aust. J. Chem., 45, 371 (1992)
Non-Patent Document 6: J. Org. Chem., 60, 7508 (1995)
Non-Patent Document 7: Synth. Commun., 11, 513 (1981)

SUMMARY OF THE INVENTION

Problems to be Solved by the Invention

Objects of the present invention are to provide an organic compound having excellent properties, which is excellent in electron-injection/transport performances, has hole-blocking ability and has high stability in a thin-film state, as a material for an organic electroluminescence device having a high efficiency and a high durability, and to provide an organic electroluminescence device having a high efficiency and a high durability using the compound.

As physical properties of the organic compound to be provided by the present invention, there may be mentioned (1) a good electron-injection characteristic, (2) a high electron mobility, (3) an excellent hole-blocking ability, (4) good stability in a thin-film state, and (5) excellent thermal resistance. In addition, as physical properties of the organic electroluminescence device to be provided by the present invention, there may be mentioned (1) high luminous efficiency and power efficiency, (2) low emission initiation voltage, (3) low practical driving voltage.

Means for Solving the Problems

Thus, in order to achieve the above objects, the present inventors have designed and chemically synthesized compounds having a benzotriazole ring structure and a pyridine ring structure, with focusing on the fact that the benzotriazole ring structure and pyridine ring structure have an excellent electron-transport performance and is excellent in thermal resistance. The present inventors have experimentally produced various organic electroluminescence devices using the compounds, and have extensively performed property evaluation of the devices. As a result, they have accomplished the present invention.

That is the present invention provides: a compound having a benzotriazole ring structure represented by the following general formula (1); and an organic electroluminescence device comprising a pair of electrodes and at least one organic layer sandwiched therebetween, wherein the device comprises the compound as a constituent material of at least one organic layer.

[Chem. 1]

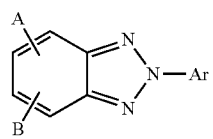

(1)

(wherein Ar represents a substituted or unsubstituted aromatic hydrocarbon group, a substituted or unsubstituted aromatic heterocyclic group, or a substituted or unsubstituted condensed polycyclic aromatic group; and A and B may be the same as or different from each other and each represent a hydrogen atom or a monovalent group represented by the following general formula (2), provided that A and B are not simultaneously hydrogen atoms).

[Chem. 2]

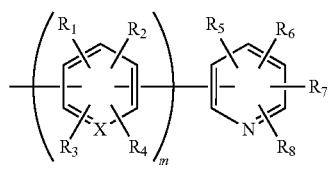

(2)

(wherein $R_1$ to $R_8$ may be the same as or different from each other and each represent a hydrogen atom, a deuterium atom, a fluorine atom, a chlorine atom, a cyano group, a trifluoromethyl group, a linear or branched alkyl group having 1 to 6 carbon atoms, a substituted or unsubstituted aromatic hydrocarbon group, a substituted or unsubstituted aromatic heterocyclic group, or a substituted or unsubstituted condensed polycyclic aromatic group; m is an integer of 0, 1 or 2; X represents a carbon atom or a nitrogen atom; when X is a nitrogen atom, the nitrogen atom does not have substituents or bonding groups of $R_1$, $R_2$, $R_3$ and $R_4$; and when m is 2, a plurality of $R_1$, $R_2$, $R_3$, $R_4$ and X each may be the same or different).

The "aromatic hydrocarbon group", the "aromatic heterocyclic group" or the "condensed polycyclic aromatic group" in the "substituted or unsubstituted aromatic hydrocarbon group", the "substituted or unsubstituted aromatic heterocyclic group", or the "substituted or unsubstituted condensed polycyclic aromatic group", represented by Ar in general formula (1), specifically includes a phenyl group, a biphenylyl group, a terphenylyl group, a naphthyl group, an anthryl group, a phenanthryl group, a fluorenyl group, an indenyl group, a pyrenyl group, a pyridyl group, a triazyl group, a pyrimidyl group, a furanyl group, a pyranyl group, a thiophenyl group, a quinolyl group, an isoquinolyl group, a benzofuranyl group, a benzothiophenyl group, an indolyl group, a carbazolyl group, a benzoxazolyl group, a benzothiazolyl group, a quinoxalyl group, a benzimidazolyl group, a pyrazolyl group, a dibenzofuranyl group, a dibenzothiophenyl group, a naphthyridinyl group, a phenanthrolinyl group and an acridinyl group.

The "substituent" in the "substituted aromatic hydrocarbon group", the "substituted aromatic heterocyclic group", or the "substituted condensed polycyclic aromatic group", represented by Ar in general formula (1), specifically includes deuterium atom, a fluorine atom, a chlorine atom, a cyano group, a hydroxyl group, a nitro group, a linear or branched alkyl group having 1 to 6 carbon atoms, a cyclopentyl group, a cyclohexyl group, a linear or branched alkoxy group having 1 to 6 carbon atoms, a dialkylamino group substituted with a linear or branched alkyl group having 1 to 6 carbon atoms, a phenyl group, a naphthyl group, an anthryl group, a fluorenyl group, a styryl group, a pyridyl group, a pyridoindolyl group, a quinolyl group and a benzothiazolyl group. These substituents may be further substituted.

The "aromatic hydrocarbon group", the "aromatic heterocyclic group" or the "condensed polycyclic aromatic group" in the "substituted or unsubstituted aromatic hydrocarbon group", the "substituted or unsubstituted aromatic heterocyclic group", or the "substituted or unsubstituted condensed polycyclic aromatic group", represented by $R_1$ to $R_8$ in general formula (2), specifically includes a phenyl group, a biphenylyl group, a terphenylyl group, a tetrakisphenyl group, a styryl group, a naphthyl group, an anthryl group, an acenaphthenyl group, a fluorenyl group, a phenanthryl group, an indenyl group, a pyrenyl group, a pyridyl group, a triazyl group, a pyrimidyl group, a furanyl group, a pyranyl group, a thiophenyl group, a quinolyl group, an isoquinolyl group, a benzofuranyl group, a benzothiophenyl group, an indolyl group, a carbazolyl group, a benzoxazolyl group, a benzothiazolyl group, a quinoxalyl group, a benzimidazolyl group, a pyrazolyl group, a dibenzofuranyl group, a dibenzothiophenyl group, a naphthyridinyl group, a phenanthrolinyl group and an acridinyl group.

The "substituent" in the "substituted aromatic hydrocarbon group", the "substituted aromatic heterocyclic group", or the "substituted condensed polycyclic aromatic group", represented by $R_1$ to $R_8$ in general formula (2), specifically includes a deuterium atom, a fluorine atom, a chlorine atom, a trifluoromethyl group, a linear or branched alkyl group having 1 to 6 carbon atoms, a phenyl group, a biphenylyl group, a terphenylyl group, a tetrakisphenyl group, a styryl group, a naphthyl group, a fluorenyl group, a phenanthryl group, an indenyl group and a pyrenyl group, and these substituents may be further substituted.

The "linear or branched alkyl group having 1 to 6 carbon atoms", represented by $R_1$ to $R_8$ in general formula (2), specifically includes a methyl group, an ethyl group, an n-propyl group, an i-propyl group, an n-butyl group, a 2-methyl-propyl group, a t-butyl group, an n-pentyl group, an 3-methyl-butyl group, a t-pentyl group, an n-hexyl group, an i-hexyl group and a t-hexyl group.

The compound having a benzotriazole ring structure and a pyridine ring structure, which is represented by general formula (1) of the present invention, is a novel compound, provides high electron mobility as compared with conventional electron-transport materials, has an excellent hole-blocking ability, and is stable in a thin-film state.

The compound having a benzotriazole ring structure and a pyridine ring structure, which is represented by general formula (1) of the present invention, can be used as a constituent material for an electron-injection layer and/or electron-transport layer of an organic electroluminescence device (hereinafter, abbreviated as organic EL device). The use of the material of the present invention, exhibiting a higher electron-injection/mobility as compared with conventional materials provides effects of improving electron-transport efficiency from the electron-transport layer to a luminescent layer to enhance luminous efficiency and also lowering a driving voltage to enhance durability of the organic EL device.

The compound having a benzotriazole ring structure and a pyridine ring structure, which is represented by general formula (1) of the present invention, can be also used as a constituent material for a hole-blocking layer of an organic EL device. The use of the material of the present invention, excellent in hole-blocking ability and also excellent in electron-transport property as compared with conventional materials and having high stability in a thin-film state provides effects of lowering a driving voltage, improving current resistance, and enhancing maximum emission luminance of the organic EL device, while exhibiting a high luminous efficiency.

The compound having a benzotriazole ring structure and a pyridine ring structure, which is represented by general formula (1) of the present invention, can be also used as a constituent material for a luminescent layer of an organic EL device. The use of a luminescent layer prepared by using the material of the present invention, excellent in electron-transport property as compared with conventional materials and having a wide band-gap as a host material for the luminescent layer, and by making a fluorescent material or a phosphorescent material, called a dopant, carried thereon provides an effect of realizing an organic EL device exhibiting a lowered driving voltage and having an improved luminous efficiency.

The organic EL device of the present invention uses the compound having a benzotriazole ring structure and a pyridine ring structure, which compound exhibits high electron mobility as compared with conventional electron-transport materials, has an excellent hole-blocking ability and is stable in a thin-film state. Therefore, it becomes possible to realize high efficiency and high durability.

Advantageous Effects of the Invention

The compound having a benzotriazole ring structure and a pyridine ring structure of the present invention is useful as a constituent material for an electron-injection layer, an electron-transport layer, a hole-blocking layer, or a luminescent layer of an organic EL device, and the compound exhibits an excellent hole-blocking ability, is stable in a thin-film state, and has excellent thermal resistance. The organic EL device of the present invention exhibits a high luminous efficiency and power efficiency, whereby the practical driving voltage of the device can be lowered. By lowering the light emission initiation voltage, the durability can be improved.

MODE FOR CARRYING OUT THE INVENTION

Figure 1:
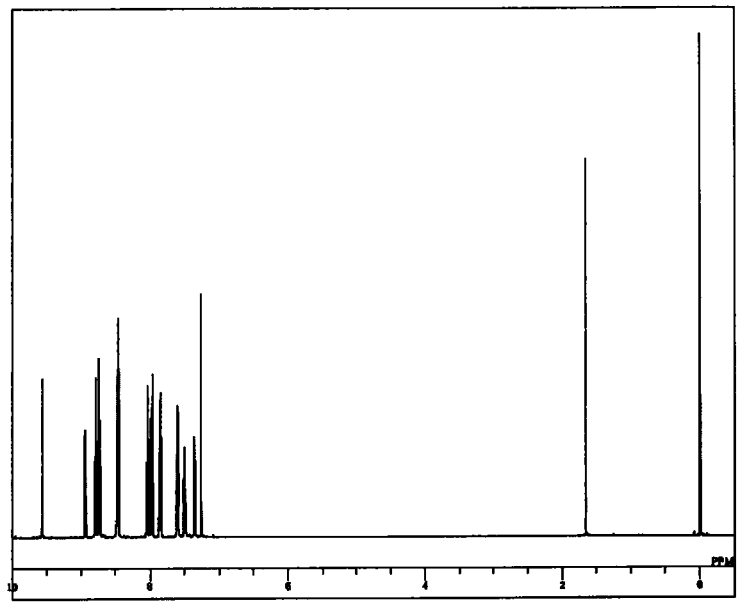
FIG. 1 is a 1H-NMR chart of the compound (Compound 11) of Invention Example 1.

The compounds having a benzotriazole ring structure and a pyridine ring structure of the present invention are a novel compound, and those compounds can be synthesized, for example, as follows. First, 2-Aminoarylazobenzene derivative is synthesized from 1,2-diaminobenezene derivative and nitroaryl derivative by the conventional method, and then subjected to a halogenation reaction, whereby the corresponding halogeno-2-aminoarylazobenzene derivative can be synthesized. The halogeno-2-aminoarylazobenzene derivative is subjected to oxidative cyclization reaction by bis(acetato-O)phenyliodine to synthesize halogeno-2-arylbenzotriazole derivative having a benzotriazole ring (for example, see Non-Patent Document 5). Boronic acid or boronic acid ester synthesized by the reaction between the halide and pinacol borane or bis(pinacol)diborane (for example, see Non-Patent Document 6) is subjected to a cross coupling reaction such as Suzuki coupling (for example, see Non-Patent Document 7) with various halogenopyridines or pyridylaryl halides, whereby a compound having a benzotriazole ring structure and a pyridine ring structure can be synthesized.

Among the compounds having a benzotriazole ring structure and a pyridine ring structure, represented by the general formula (1), specific examples of the preferred compounds are shown below, but the present invention is not limited to those compounds.

[Chem.3]

(Compound 3)

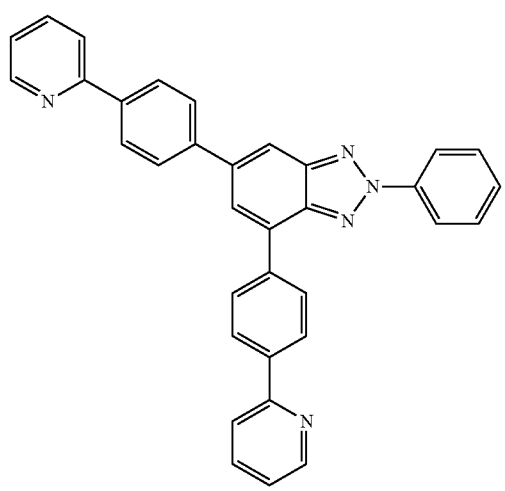

[Chem.4]
(Compound 4)
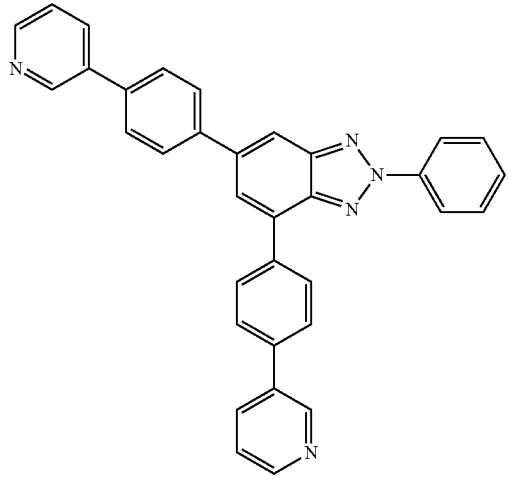
[Chem. 5]
(Compound 5)
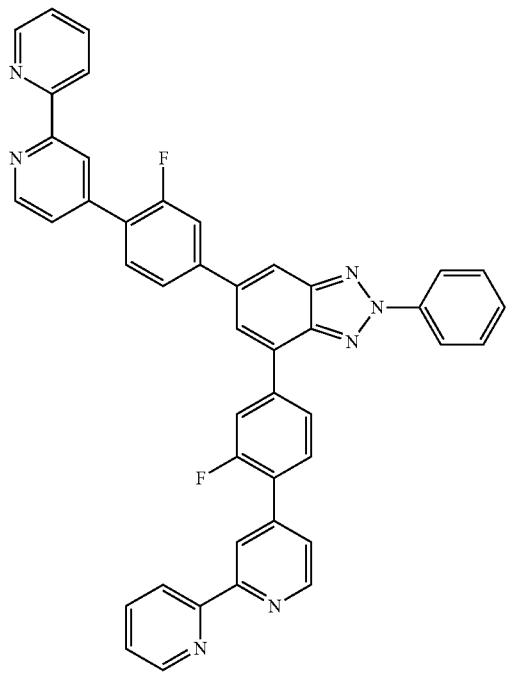

-continued
[Chem. 6]
(Compound 6)
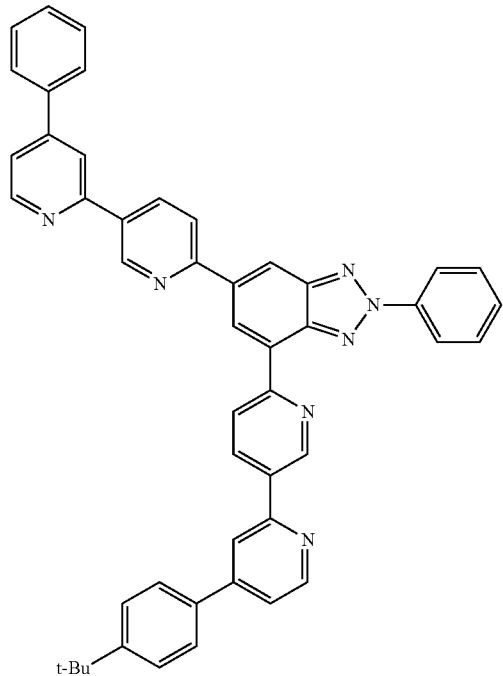
[Chem. 7]
(Compound 7)
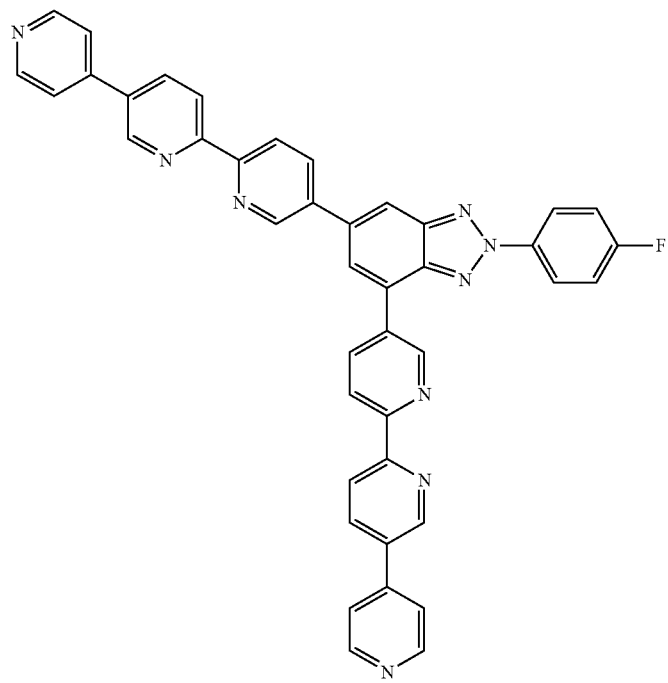

-continued
[Chem.8]
(Compound 8)
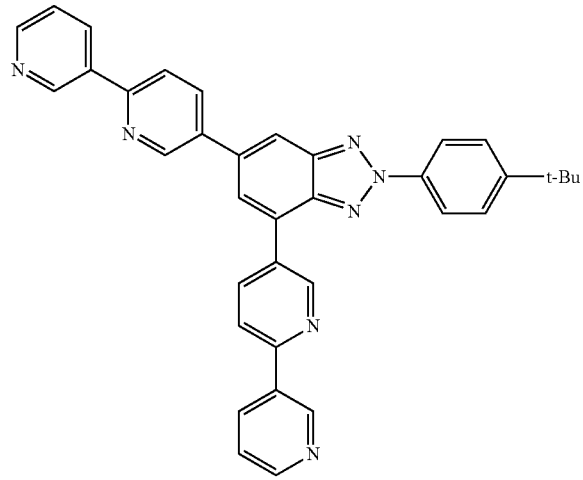
[Chem.9]
(Compound 9)
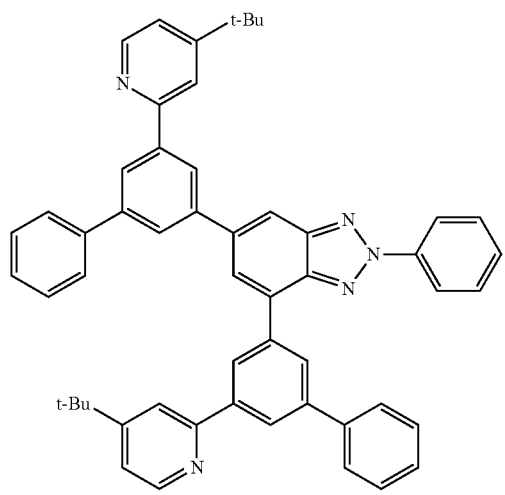
[Chem. 10]
(Compound 10)
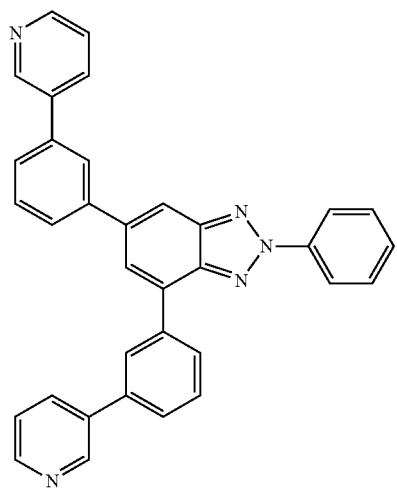

-continued
[Chem. 11]
(Compound 11)
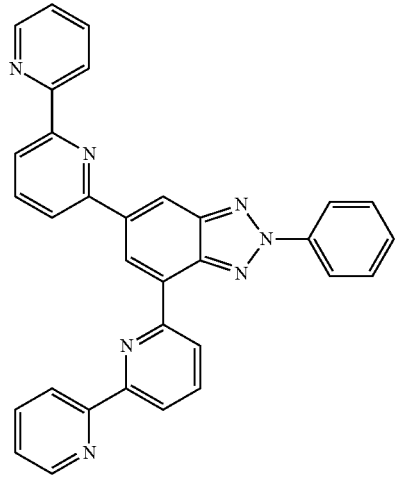
[Chem. 12]
(Compound 12)
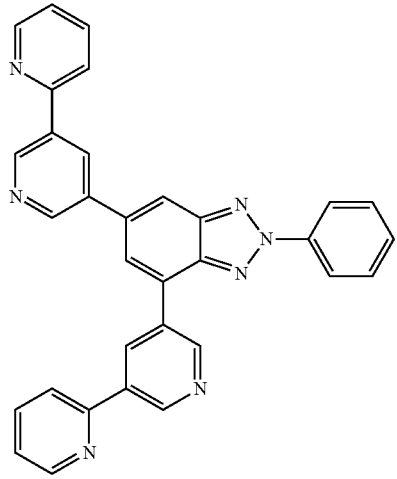
[Chem. 13]
(Compound 13)
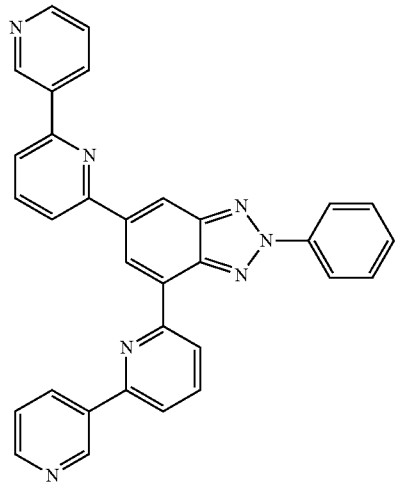

-continued
[Chem. 14]
(Compound 14)
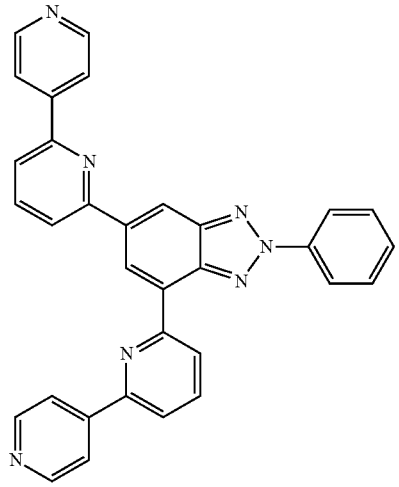
[Chem. 15]
(Compound 15)
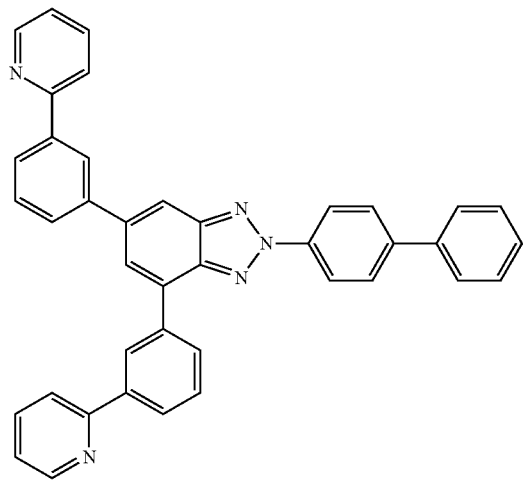
[Chem. 16]
(Compound 16)
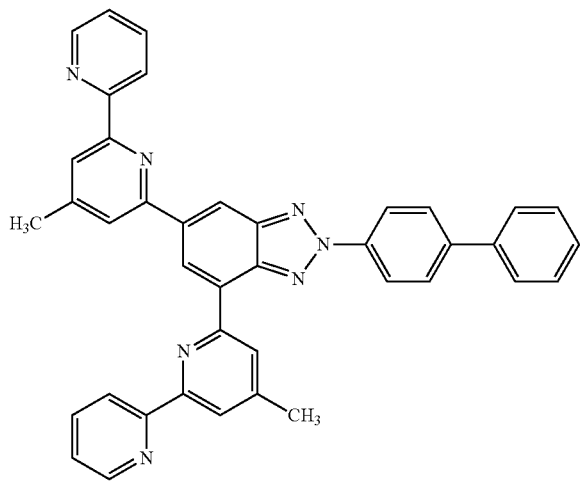

-continued
[Chem. 17]
(Compound 17)
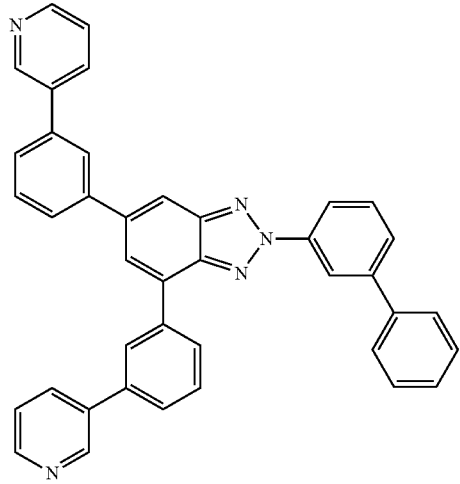
[Chem. 18]
(Compound 18)
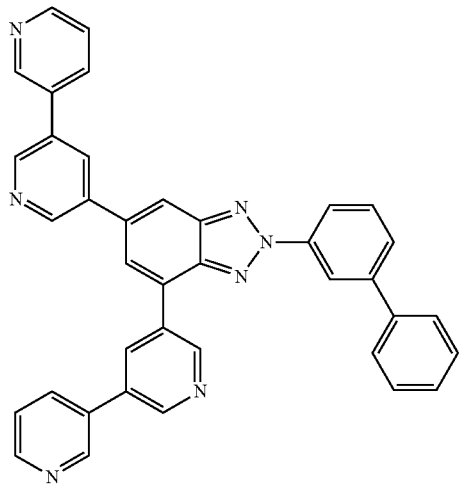
[Chem. 19]
(Compound 19)
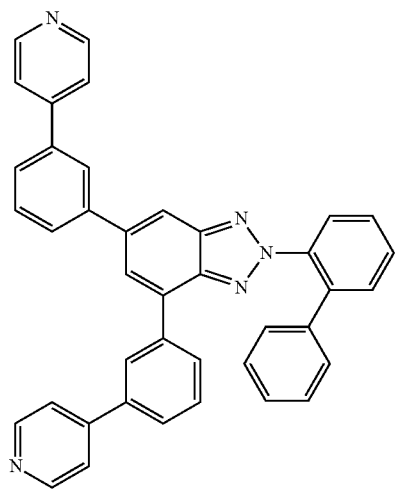

[Chem. 20]
(Compound 20)
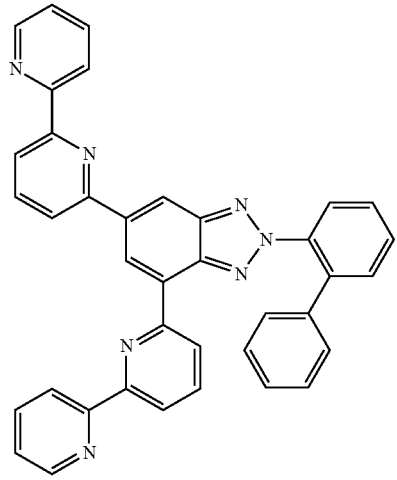
[Chem. 21]
(Compound 21)
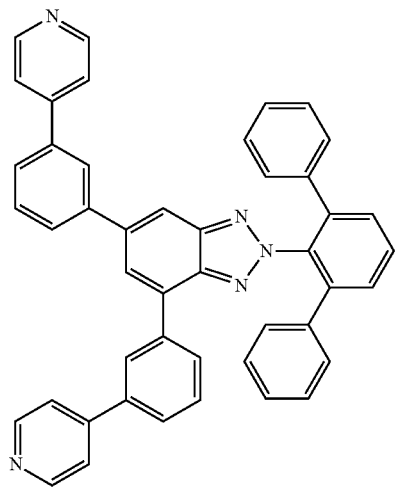
[Chem. 22]
(Compound 22)
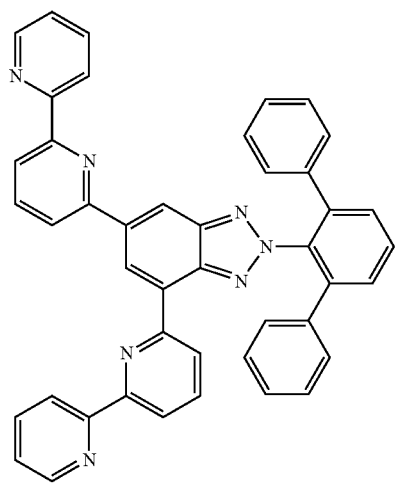

[Chem. 23]
(Compound 23)
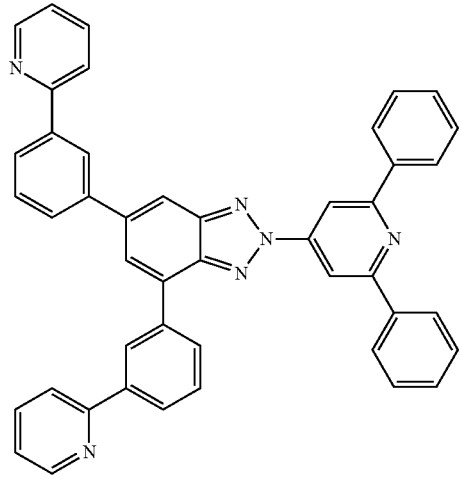
[Chem. 24]
(Compound 24)
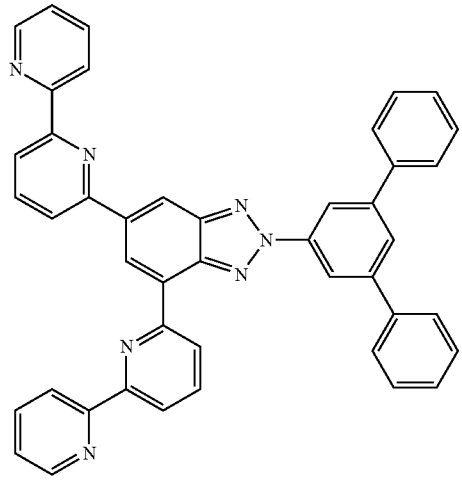
[Chem. 25]
(Compound 25)
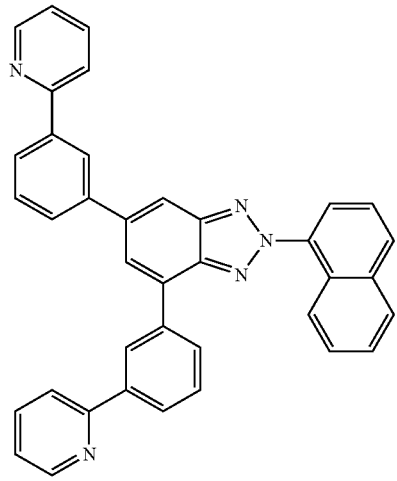

-continued
[Chem. 26]
(Compound 26)
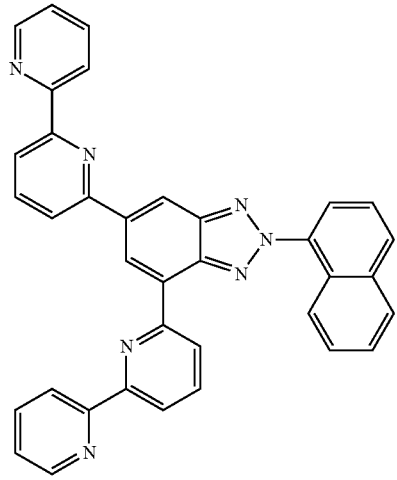
[Chem. 27]
(Compound 27)
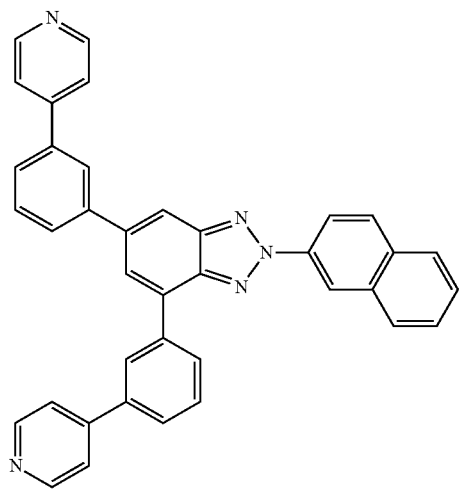

-continued
[Chem. 28]
(Compound 28)
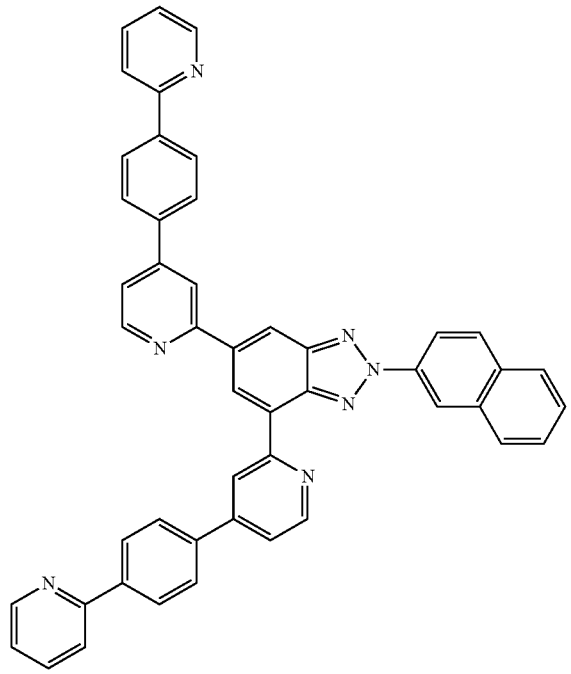
[Chem. 29]
(Compound 29)
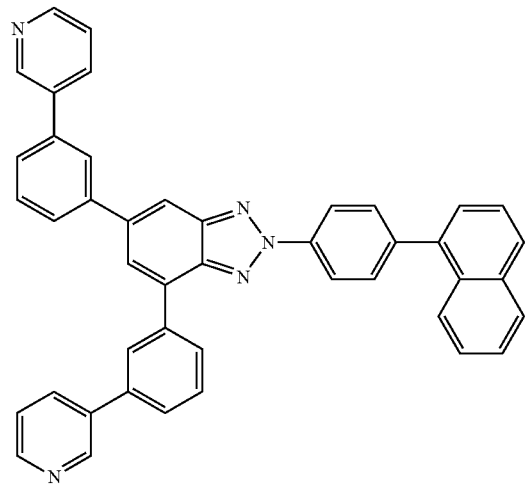

[Chem. 30]
(Compound 30)
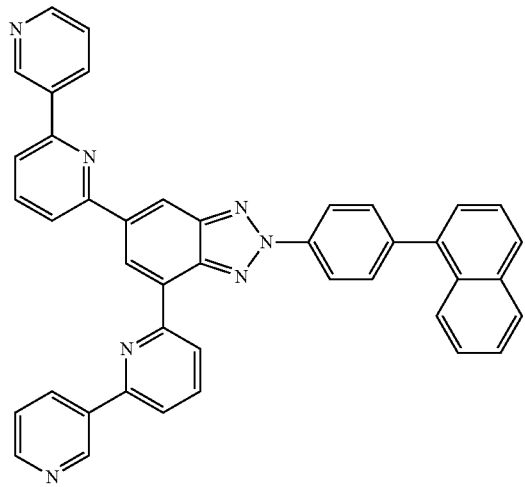
[Chem. 31]
(Compound 31)
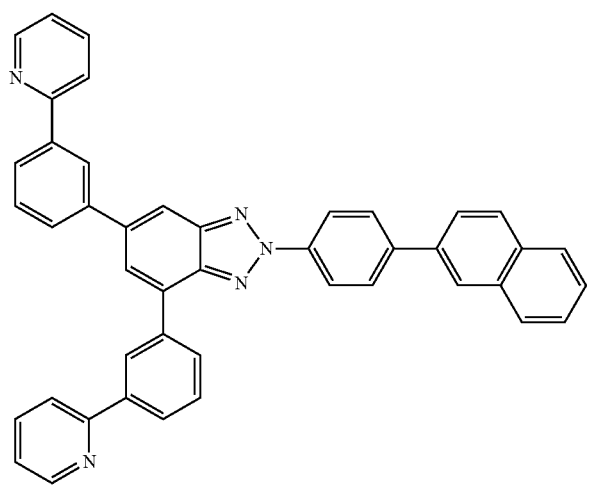
[Chem. 32]
(Compound 32)
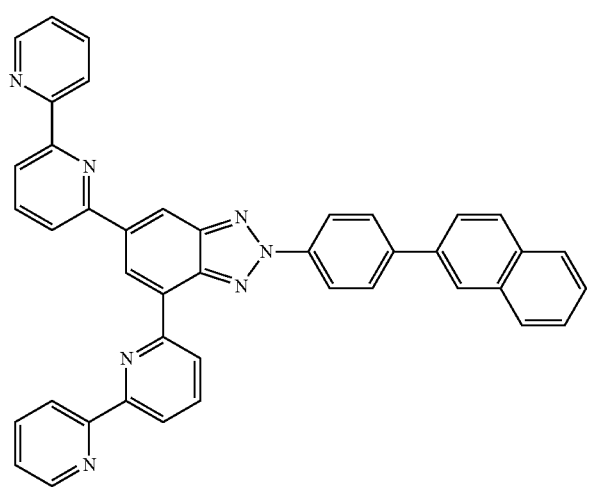

[Chem. 33]
(Compound 33)
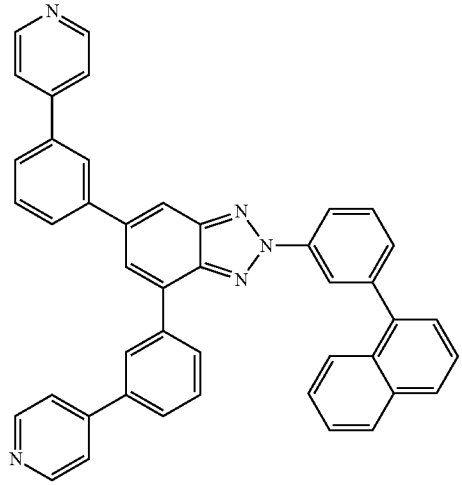
[Chem. 34]
(Compound 34)
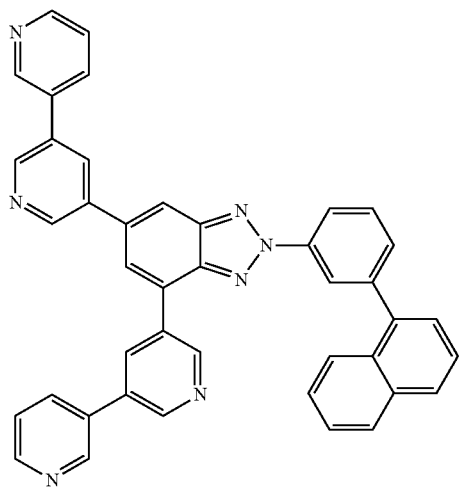
[Chem. 35]
(Compound 35)
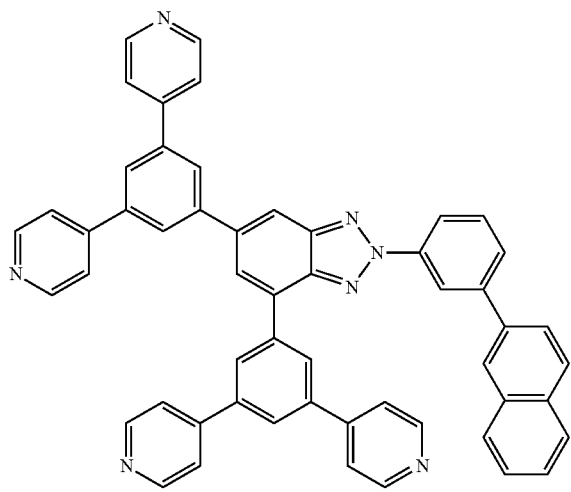

[Chem. 36]
(Compound 36)
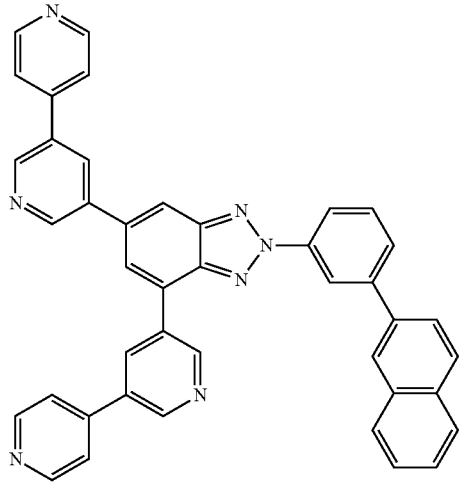
[Chem. 37]
(Compound 37)
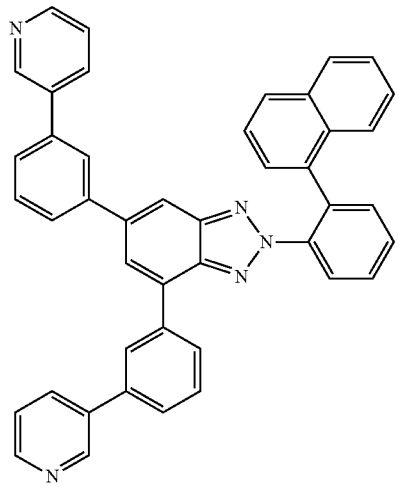
[Chem. 38]
(Compound 38)
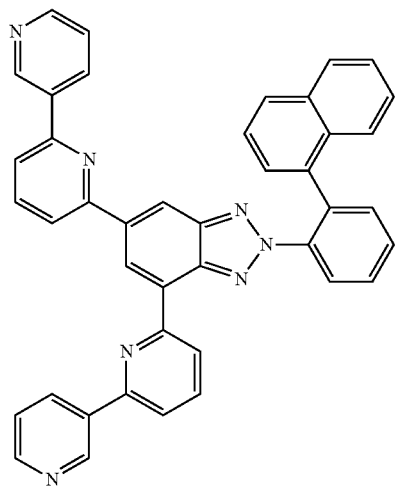

[Chem. 39]
(Compound 39)
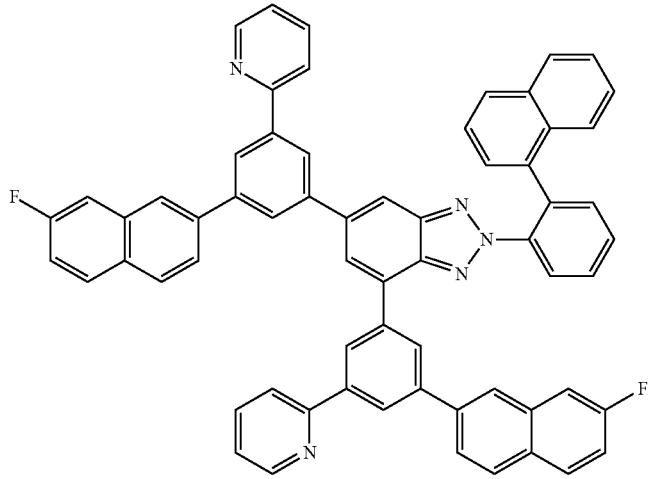
[Chem. 40]
(Compound 40)
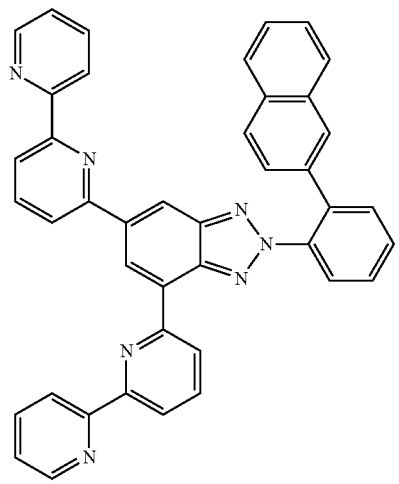
[Chem. 41]
(Compound 41)
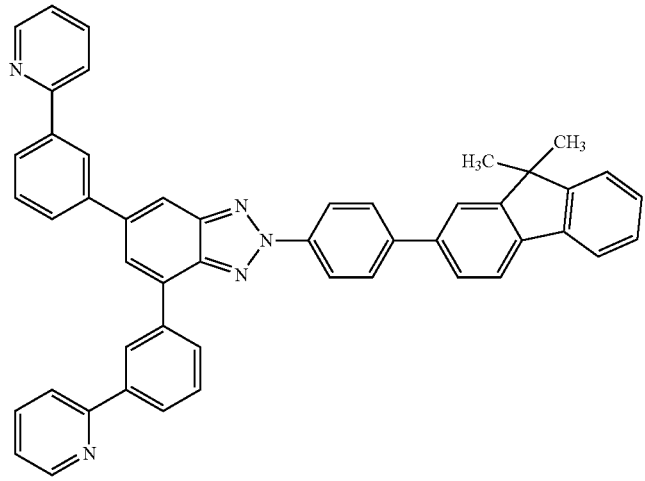

-continued
[Chem. 42]
(Compound 42)
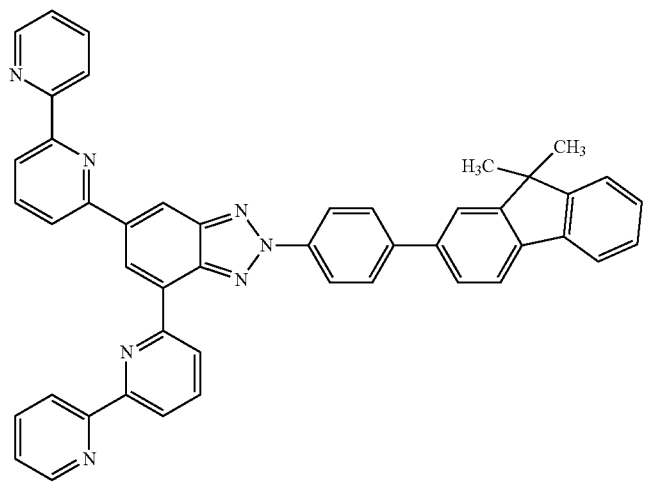
[Chem. 43]
(Compound 43)
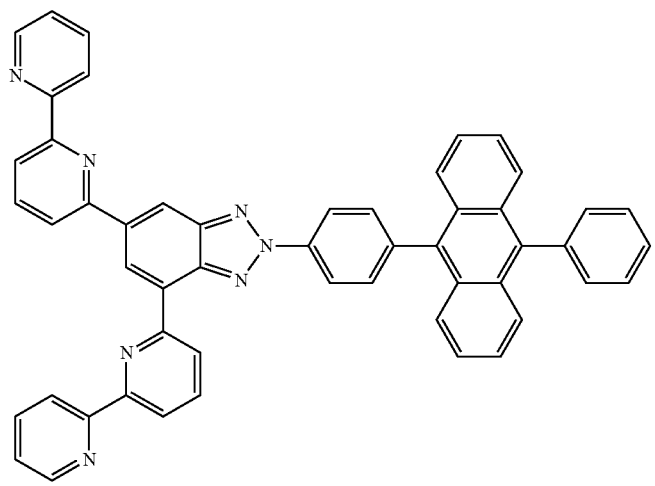
[Chem. 44]
(Compound 44)
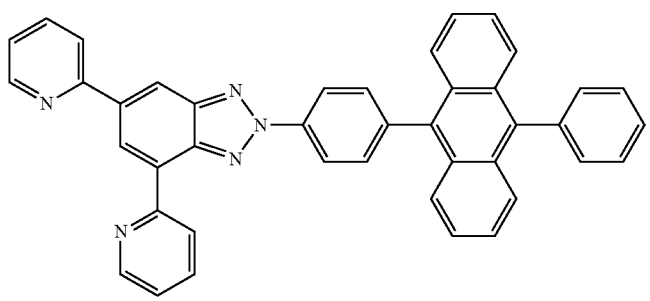

-continued
[Chem. 45]
(Compound 45)
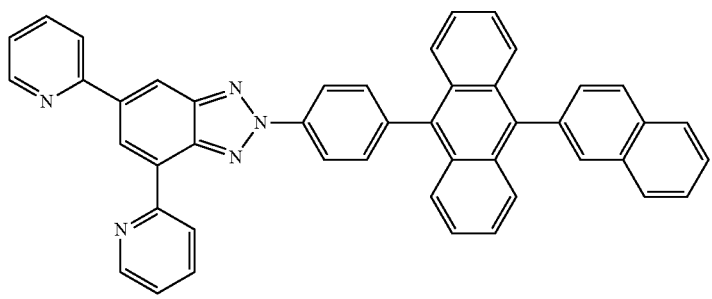
[Chem. 46]
(Compound 46)
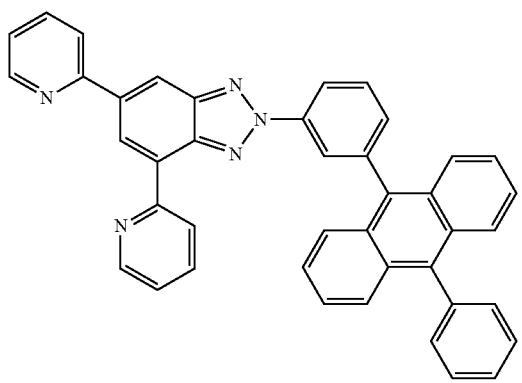
[Chem. 47]
(Compound 47)
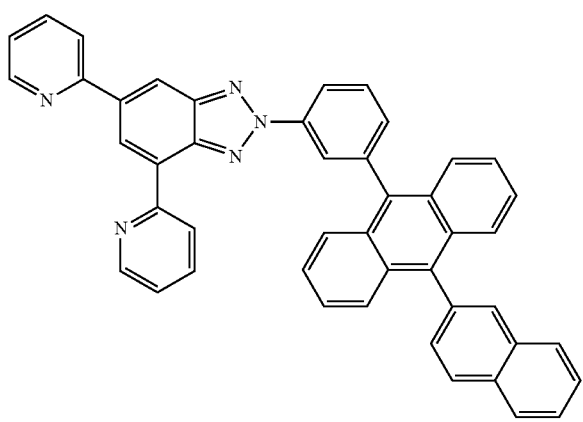
[Chem. 48]
(Compound 48)
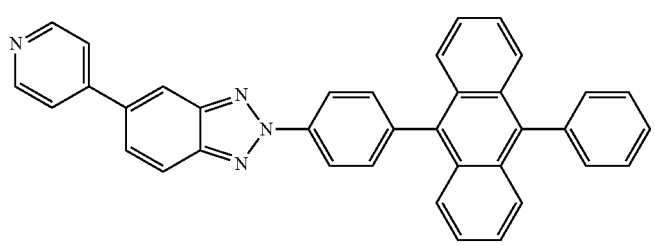

[Chem. 49]
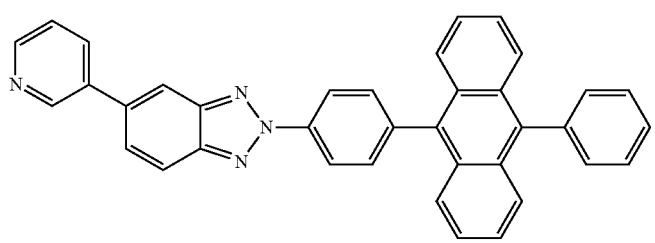
(Compound 49)
[Chem 50]
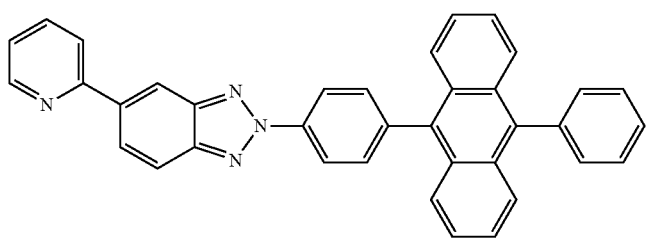
(Compound 50)
[Chem 51]
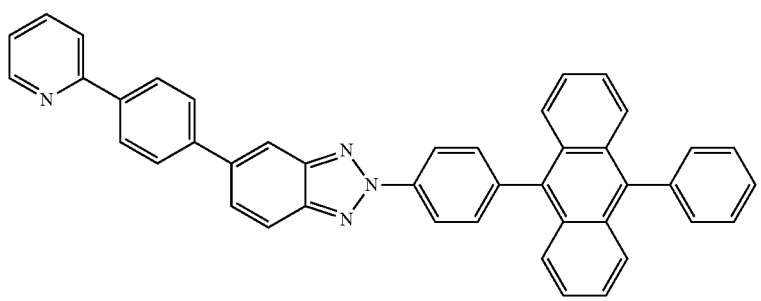
(Compound 51)
[Chem 52]
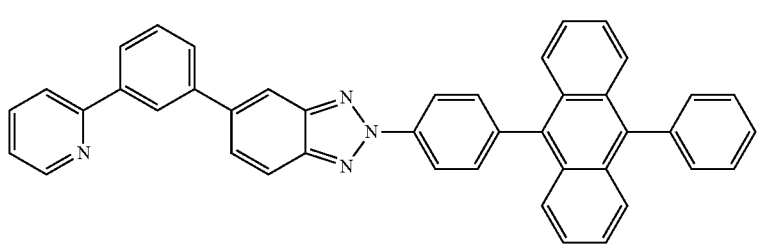
(Compound 52)
[Chem 53]
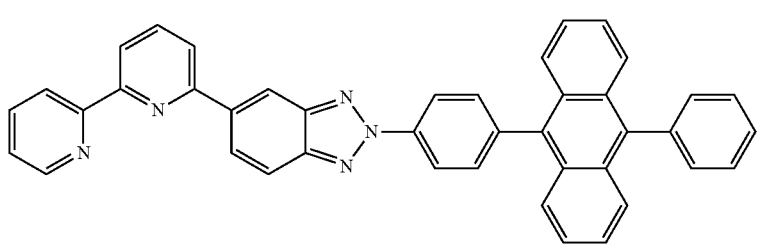
(Compound 53)

[Chem. 54]
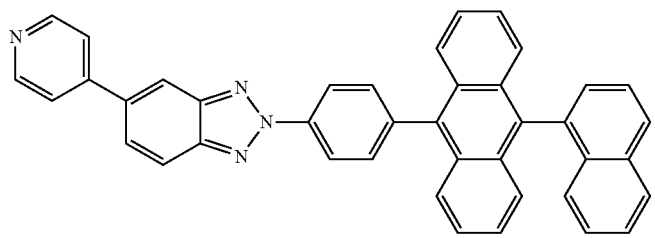
(Compound 54)
[Chem. 55]
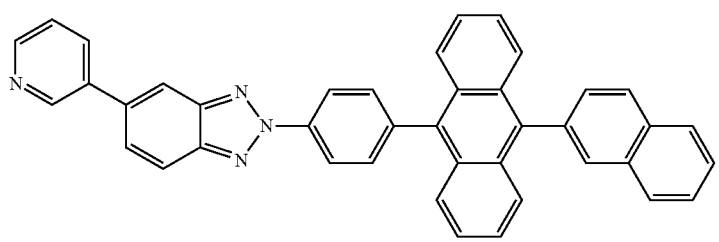
(Compound 55)
[Chem. 56]
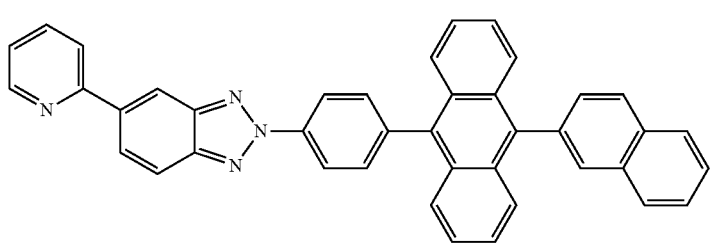
(Compound 56)
[Chem. 57]
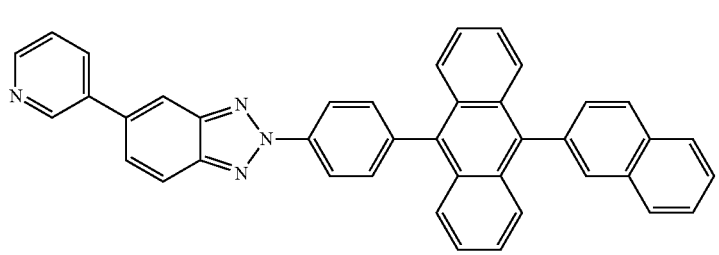
(Compound 57)
[Chem. 58]
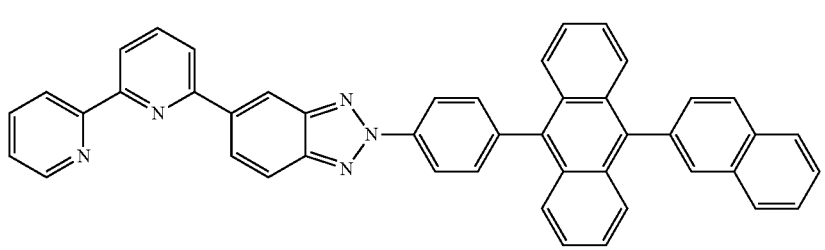
(Compound 58)

-continued
[Chem. 59]
(Compound 59)
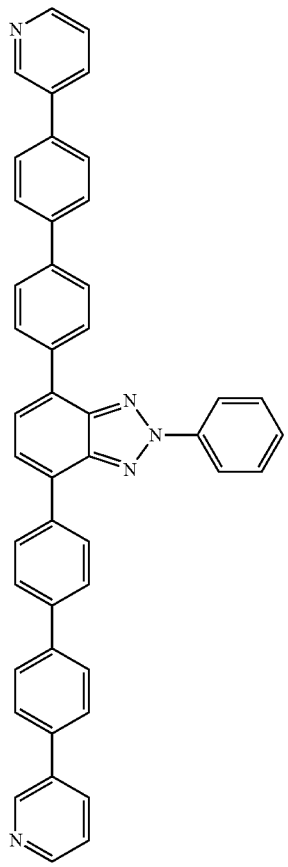
[Chem. 60]
(Compound 60)
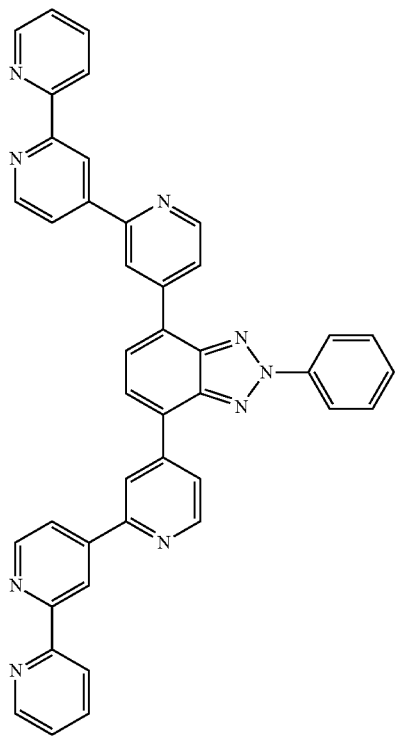

-continued
[Chem. 61]
(Compound 61)
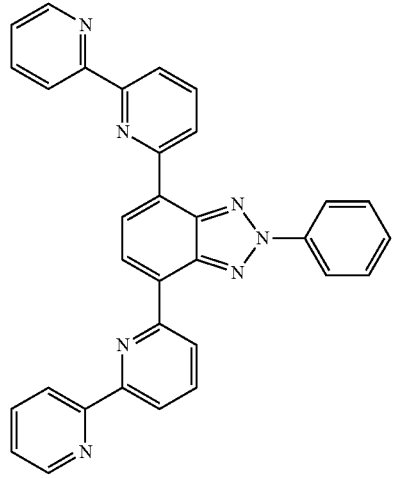
[Chem. 62]
(Compound 62)
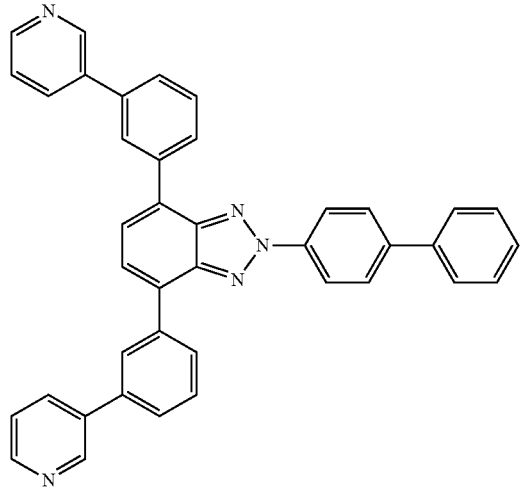
[Chem. 63]
(Compound 63)
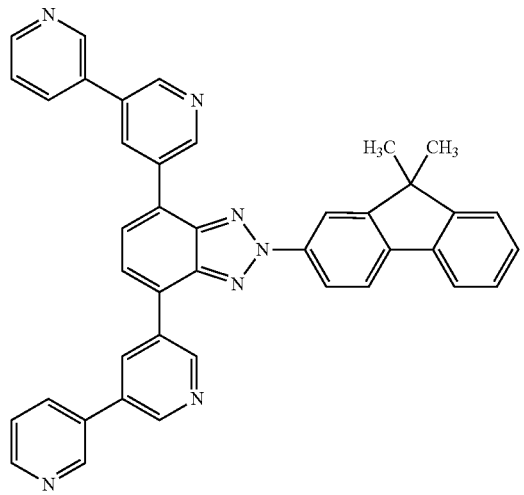

-continued
[Chem. 64]
(Compound 64)
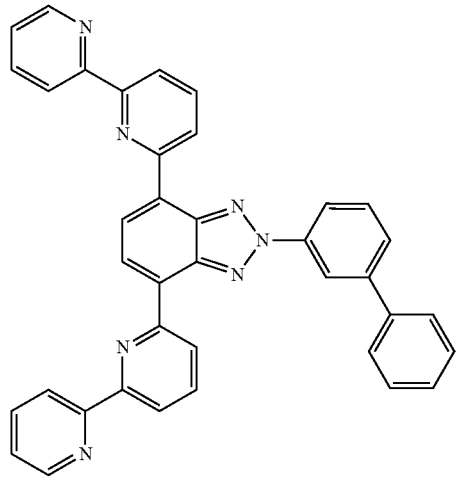
[Chem. 65]
(Compound 65)
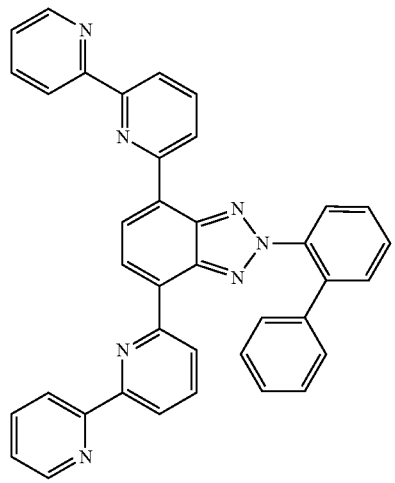
[Chem. 66]
(Compound 66)
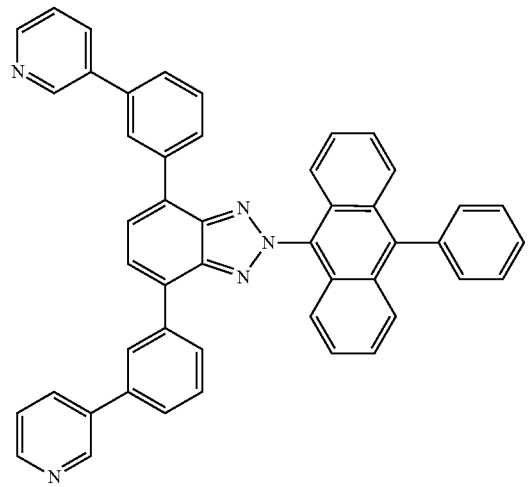

[Chem. 67]
(Compound 67)
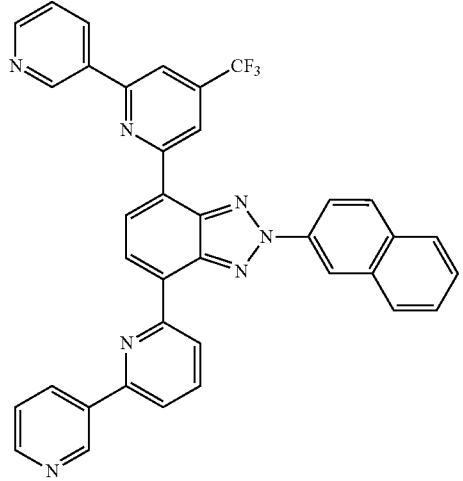
[Chem. 68]
(Compound 68)
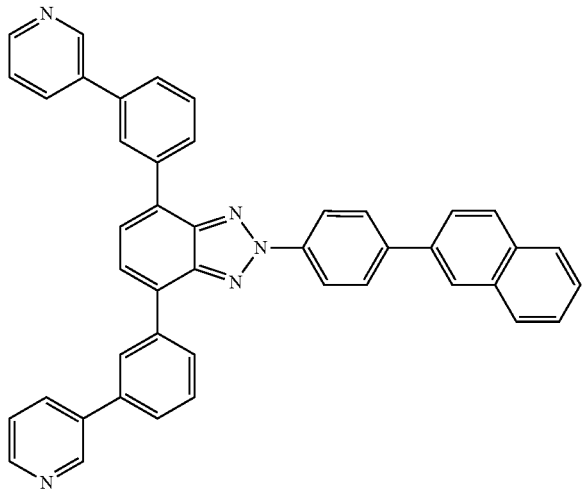
[Chem. 69]
(Compound 69)
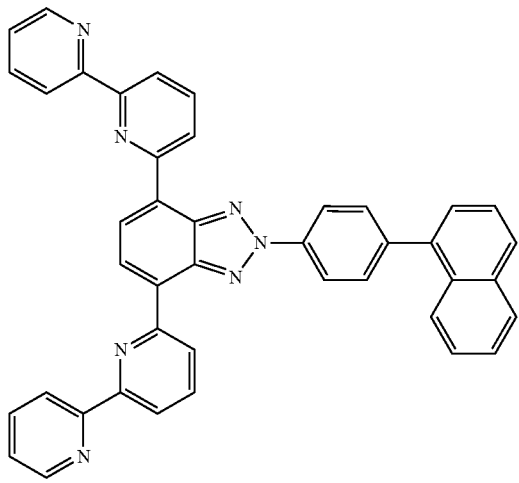

[Chem. 70]
(Compound 70)
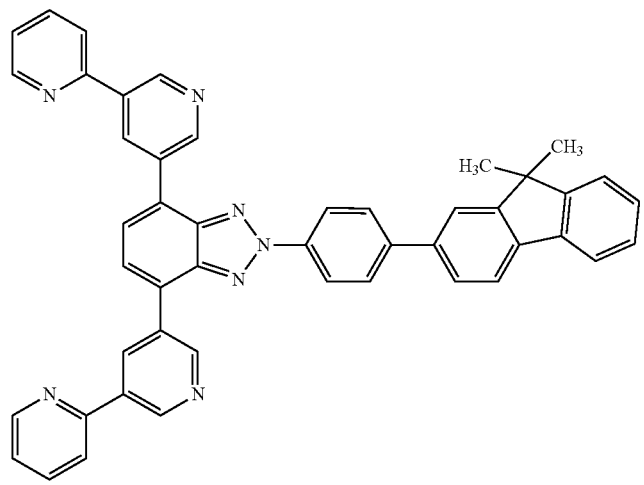
[Chem. 71]
(Compound 71)
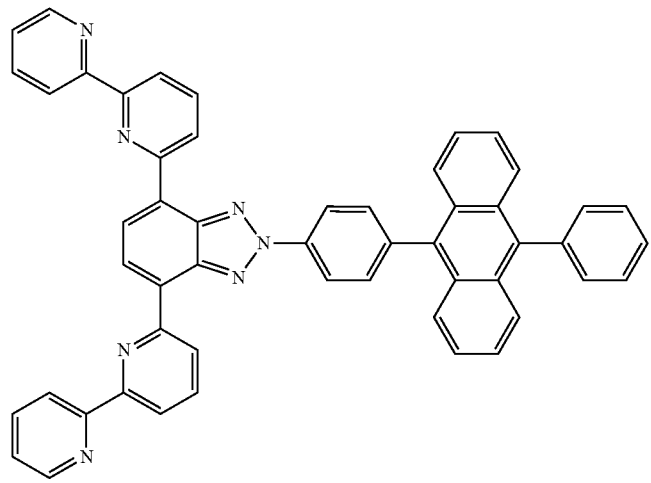
[Chem. 72]
(Compound 72)
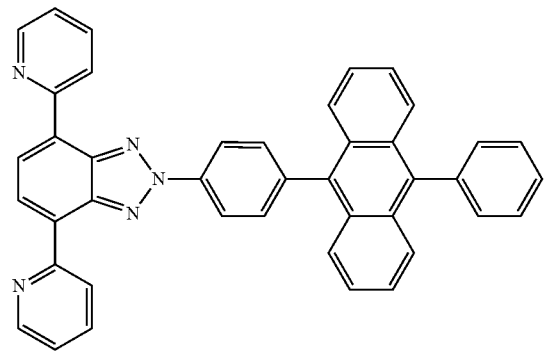

[Chem. 73]
(Compound 73)
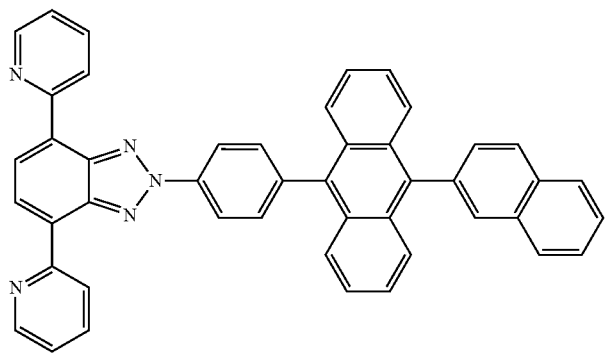
[Chem. 74]
(Compound 74)
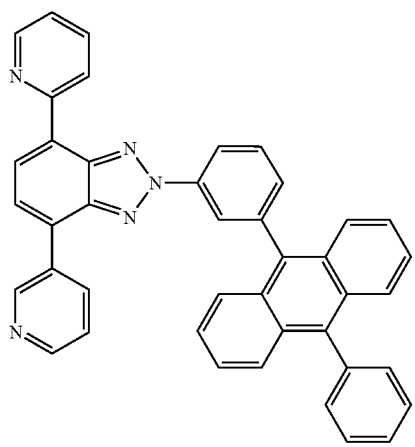
[Chem. 75]
(Compound 75)
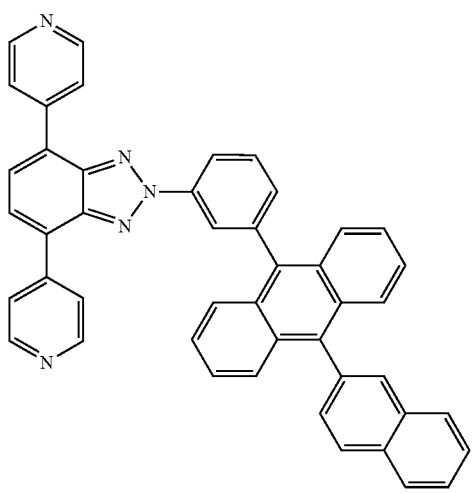

[Chem. 76]
(Compound 76)
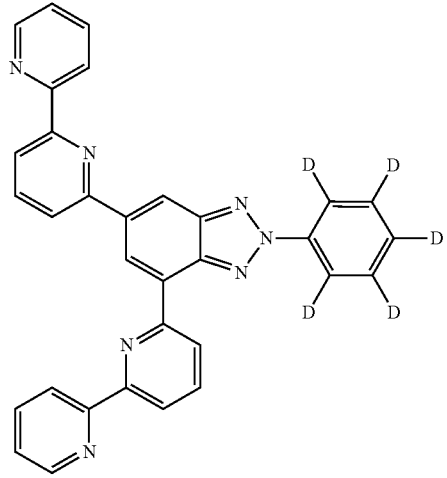
[Chem. 77]
(Compound 77)
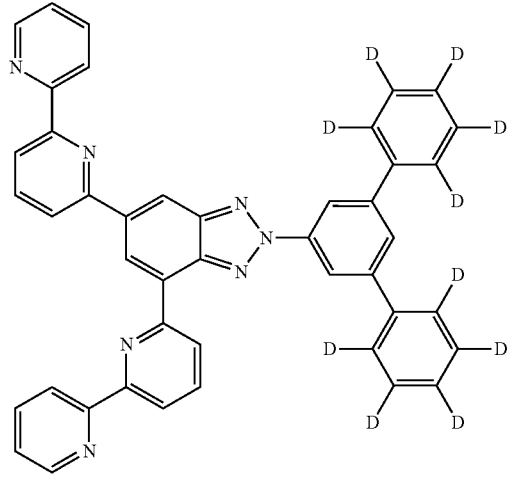
[Chem. 78]
(Compound 78)
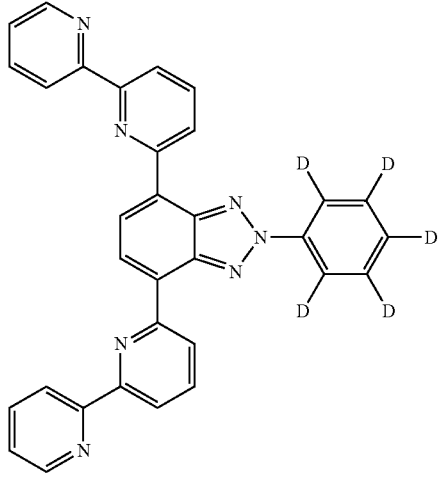

-continued

[Chem. 79]

(Compound 79)

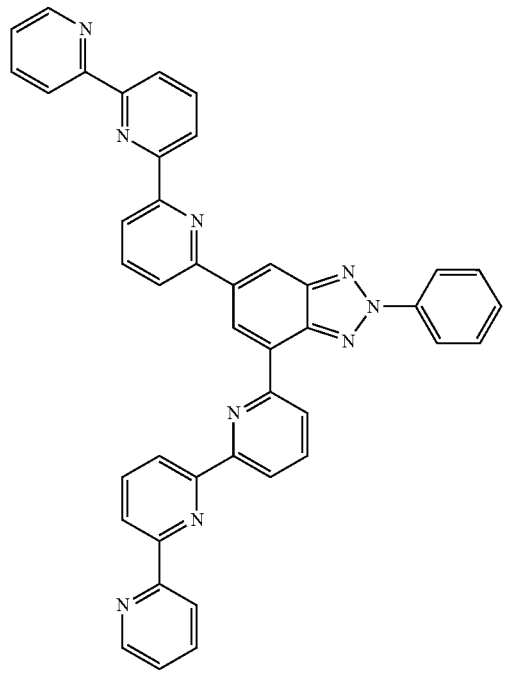

[Chem. 80]

(Compound 80)

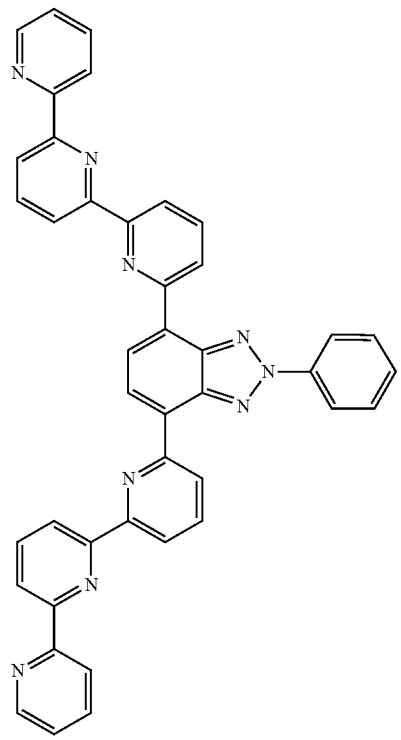

Purification of these compounds was performed by purification by column chromatography, adsorption purification with silica gel, active carbon, activated clay, or the like, a recrystallization or crystallization method with a solvent, or the like. Identification of the compounds was performed by NMR analysis. As physical properties, glass transition point (Tg) and melting point measurement were carried out with DSC measurement. The melting point serves as an indicator of vapor deposition properties, and the glass transition point (Tg) serves as an indicator of stability in a thin-film state. The compound having a melting point of 200° C. or more is preferred.

The melting point and the glass transition point were measured using a powder material by means of a highly sensitive differential scanning calorimeter DSC 6200 manufactured by Seiko Instruments Inc.

Further, the work function was measured by preparing a thin film of 100 nm on an ITO substrate and by using an atmospheric photoelectron spectroscopy AC-3 manufactured by Riken Keiki Co., Ltd. The work function serves as an indicator of hole-blocking ability.

Examples of the structure of the organic EL device of the present invention include: a structure having an anode, a hole-transport layer, a luminescent layer, a hole-blocking layer, an electron-transport layer and a cathode in this order on a substrate; a structure further having a hole-injection layer between the anode and the hole transport layer; and a structure further having an electron-injection layer between the electron-transport layer and the cathorde. In these multilayer structures, it is possible to omit several layers of the organic layers and, for example, the structure may have a constitution sequentially having an anode, a hole-transport layer, a luminescent layer, an electron-transport layer and a cathode on a substrate.

As the anode of the organic EL device, an electrode material having a large work function, such as ITO or gold, is used. As the hole-injection layer, other than copper phthalocyanine (hereinafter, simply referred to as CuPc), materials such as starburst-type triphenylamine derivatives, and coat-type materials may be used.

For the hole-transport layer, benzidine derivatives such as N,N'-diphenyl-N,N'-di(m-tolyl)-benzidine (hereinafter, simply referred to as TPD) and N,N'-diphenyl-N,N'-di(α-naphthyl)-benzidine (hereinafter, simply referred to as NPD), various triphenylamine tetramers, and the like may be used. Also, for the hole-injection/transport layer, coat-type polymer materials such as poly(3,4-ethylenedioxythiophene) (hereinafter, simply referred to as PEDOT)/poly(styrene sulfonate) (hereinafter, simply referred to as PSS) may be used.

As for the luminescent layer, hole-blocking layer, and electron-transport layer of the organic EL device of the present invention, other than the compound having a benzotriazole ring structure and a pyridine ring structure, a compound having hole-blocking action, exemplified by aluminum complexes such as BAlq, thiazole derivatives, oxazole derivatives, carbazole derivatives, polydialkylfluorene derivatives, phenanthroline derivatives such as BCP, and triazole derivatives such as TAZ, may be used.

A conventional luminescent material such as aluminum complexes and styryl derivatives is used for the luminescent layer and the compound having a benzotriazole ring structure and a pyridine ring structure of the present invention is used for the hole-blocking layer or electron-transport layer, whereby a high-performance organic EL device can be produced. Also, a fluorescent material such as quinacridone, coumarin and rubrene can be used as the host material of the luminescent layer. As the phosphorescent material, for example, green phosphorescent materials such as phenylpyridine iridium complexes Ir(ppy)$_3$, blue phosphorescent materials such as FIrpic and FIr6, and red phosphorescent materials such as Btp$_2$Ir(acac), are used. As the host material at this time, for example, carbazole derivatives such as 4,4'-di(N-carbazolyl)biphenyl (hereinafter, simply referred to as CBP), 4,4',4''-tri(N-carbazolyl)triphenylamine (hereinafter, simply referred to as TCTA) and 1,3-bis(carbazol-9-yl)benzene (hereinafter, simply referred to as mCP) can be used as a hole-injecting/transporting host material, and such as 2,2', 2''-(1,3,5-phenylene)-tris(1-phenyl-1H-benzimidazole) (hereinafter, simply referred to as TPBI) can be used as an electron-transporting host material, whereby a high-performance organic EL device can be produced.

Furthermore, the compound having a benzotriazole ring structure and a pyridine ring structure of the present invention can be used as the electron-transport layer through multilayering or co-deposition with conventional electron-transport material(s).

The organic EL device of the present invention may have an electron-injection layer. As the electron-injection layer, lithium fluoride or the like may be used. For the cathode, an electrode material having a low work function such as aluminum, or an alloy having a lower work function such as aluminum magnesium is used as the electrode material.

Embodiments of the invention will be illustrated in greater detail with reference to the following Examples, but the invention should not be construed as being limited thereto.

EXAMPLE 1

Synthesis of 4,6-bis(2,2'-bipyridin-6-yl)-2-phenyl-2H-benzotriazole (Compound 11)

A reaction vessel substituted with nitrogen was charged with 7.6 g of 4,6-dibromo-2-phenyl-2H-benzotriazole which can be synthesized from 2,4-dibromo-6-phenylazobenzene amine (for example, see Non-Patent Document 5), 13.7 g of bis(pinacolato)diboron, 13.2 g of potassium acetate, 160 ml of dioxane (previously dehydrated with Molecular Sieve 4A) and 1.1 g of PdCl$_2$(dppf)-CH$_2$Cl$_2$, and the resulting mixture was heated and stirred at 80° C. for 72 hours. After cooling to room temperature, the reaction liquid was added to 500 ml of water, followed by stirring for 30 minutes. Precipitates were removed by filtration, and the filtrate was extracted with ethyl acetate. The organic layer was dehydrated with anhydrous magnesium sulfate, and then concentrated, thereby obtaining a crude product. The crude product was purified with column chromatograph (carrier: silica gel, eluent: toluene/ethyl acetate), thereby obtaining 6.7 g of 2-phenyl-4,6-bis(4,4,5,5-tetramethyl-[1,3,2-dioxaborolan-2-yl]-2H-benzotriazole as a yellow powder (yield: 70%).

A reaction vessel substituted with nitrogen was charged with 4.0 g of the above 2-phenyl-4,6-bis(4,4,5,5-tetramethyl-[1,3,2]-dioxaborolan-2-yl)-2H-benzotriazole, 5.0 g of 6-bromo-[2,2']-bipyridine, 13.4 ml of 2M potassium carbonate aqueous solution, 0.5 g of tetrakis(triphenyl-phosphine) palladium (0), 160 ml of toluene and 40 ml of ethanol, and the resulting mixture was refluxed under heating for 5 hours while stirring. After cooling to room temperature, 100 ml of water and 100 ml of toluene were added to separate the liquid, and an organic layer was further washed with 100 ml of water. The organic layer was dehydrated with anhydrous magnesium sulfate, and then concentrated, thereby obtaining a crude product. The crude product was purified with column chromatograph (carrier: NH silica gel, eluent: toluene), thereby obtaining 3.8 g of 4,6-bis(2,2'-bipyridin-6-yl)-2-phenyl-2H-benzotriazole (Compound 11) as a yellow powder (yield: 84%).

A structure of the thus-obtained yellow powder was identified with NMR. $^1$H-NMR measurement results are shown in FIG. 1.

The following 21 hydrogen signals were detected by $^1$H-NMR (CDCl$_3$). δ (ppm)=9.57 (1H), 8.95 (1H), 8.79 (2H), 8.74 (3H), 8.47 (4H), 8.00 (3H), 7.85 (2H), 7.60 (2H), 7.50 (1H), and 7.36 (2H)

EXAMPLE 2

Synthesis of 4,6-bis(2,2'-bipyridin-6-yl)-2-(biphenyl-2-yl)-2H-benzotriazole (Compound 20)

A reaction vessel substituted with nitrogen was charged with 10.9 g of 4,6-dibromo-2-(biphenyl-2-yl)-2H-benzotriazole which can be synthesized from 2,4-dibromo-6-(biphenyl-2-ylazo)benzene amine (for example, see Non-Patent Document 5), 15.5 g of bis(pinacolato)diboron, 15.0 g of potassium acetate, 250 ml of dioxane (previously dehydrated with Molecular Sieve 4A) and 1.3 g of $PdCl_2(dppf) \cdot CH_2Cl_2$, and the resulting mixture was heated and stirred at 90° C. for 7 hours. After cooling to room temperature, the reaction liquid was added to 500 ml of water, followed by stirring for 30 minutes. Precipitates were removed by filtration, and the filtrate was extracted with chloroform. The organic layer was dehydrated with anhydrous magnesium sulfate, and then concentrated, thereby obtaining a crude product. The crude product was purified with column chromatograph (carrier: silica gel, eluent: hexane/ethyl acetate), thereby obtaining 8.6 g of 2-(biphenyl-2-yl)-4,6-bis(4,4,5,5-tetramethyl-[1,3,2]-dioxaborolan-2-yl)-2H-benzotriazole as a green-white powder (yield: 66%).

A reaction vessel substituted with nitrogen was charged with 4.0 g of the above 2-(biphenyl-2-yl)-4,6-bis(4,4,5,5-tetramethyl-[1,3,2]dioxaborolan-2-yl)-2H-benzotriazole, 4.3 g of 6-bromo-[2,2']-bipyridine, 11.5 ml of 2M potassium carbonate aqueous solution, 0.4 g of tetrakis(triphenylphosphine)palladium (0), 80 ml of toluene, and 20 ml of ethanol, and the resulting mixture was refluxed under heating for 6 hours while stirring. After cooling to room temperature, 100 ml of water and 100 ml of toluene were added to separate the liquid, and an organic layer was further washed with 100 ml of water. The organic layer was dehydrated with anhydrous magnesium sulfate, and then concentrated, thereby obtaining a crude product. The crude product was purified with column chromatograph (carrier: NH silica gel, eluent: toluene), thereby obtaining 3.2 g of 4,6-bis(2,2'-bipyridin-6-yl)-2-(biphenyl-2-yl)-2H-benzotriazole (Compound 20) as a white powder (yield: 73%).

Figure 2:
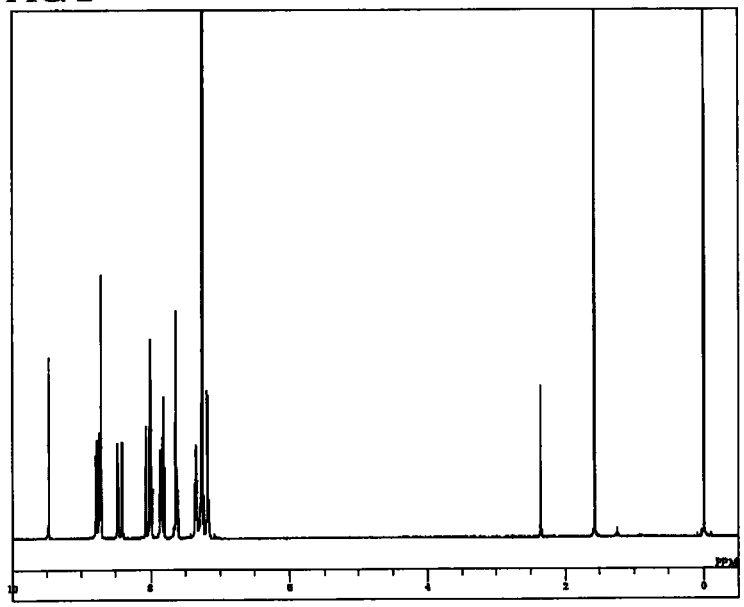
FIG. 2 is a 1H-NMR chart of the compound (Compound 20) of Invention Example 2.

A structure of the thus-obtained white powder was identified with NMR. $^1$H-NMR measurement results are shown in FIG. 2.

The following 25 hydrogen signals were detected by $^1$H-NMR (CDCl$_3$). δ (ppm)=9.48 (1H), 8.80 (1H), 8.72 (4H), 8.48 (1H), 8.42 (1H), 8.07 (1H), 8.00 (3H), 7.84 (3H), 7.64 (3H), 7.35 (2H), 7.28 (2H), and 7.18 (3H)

EXAMPLE 3

Melting points and glass transition points of the compounds of Invention Examples 1 and 2 were measured by a high sensitivity differential scanning calorimeter (DSC6200; a product of Seiko Instruments Inc.).

|  | Melting Point | Glass Transition Point |
| --- | --- | --- |
| Compound of Invention Example 1 | 230° C. | 78° C. |
| Compound of Invention Example 2 | 235° C. | 87° C. |

The compounds of the present invention show glass transition points higher than 70° C., and thin film state is stable.

EXAMPLE 4

A vapor deposition film having a film thickness of 100 nm was formed on an ITO substrate using each of the compounds of Examples 1 and 2 of the present invention, and work functions thereof were measured with an atmospheric photoelectron spectrometer (AC-3, a product of Riken Keiki Co., Ltd.).

|  | Work Function |
| --- | --- |
| Compound of Invention Example 1 | 5.92 eV |
| Compound of Invention Example 2 | 6.06 eV |

As seen above, the compounds of the present invention have values larger than the work function of 5.4 eV possessed by a general hole-transport material such as NPD and TPD, and further have values larger than 5.8 eV possessed by Alq$_3$. Thus, the compounds have large hole-blocking property.

EXAMPLE 5

Figure 3:
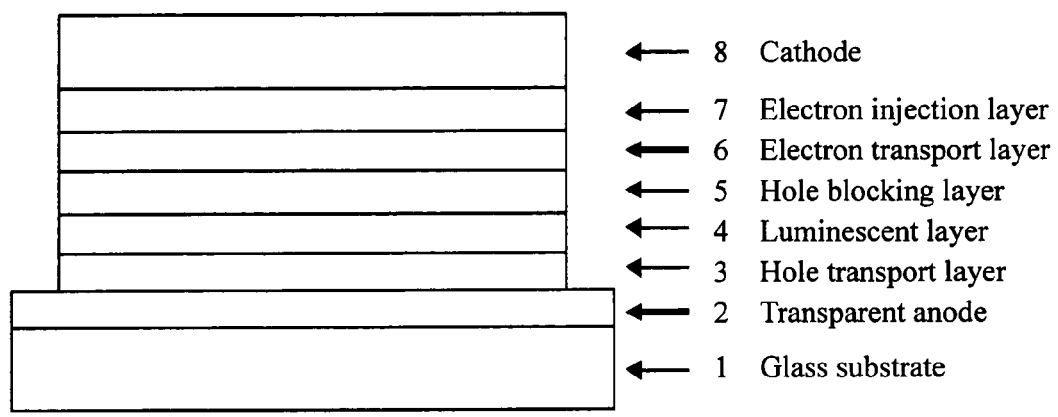
FIG. 3 is a drawing showing the constitution of the EL devices of Examples 5 to 8, and Comparative Examples 1 and 2.

As shown in FIG. 3, an organic EL device was produced by vapor-depositing a hole-transport layer 3, a luminescent layer 4, a hole-blocking layer 5, an electron-transport layer 6, an electron-injection layer 7 and a cathode (aluminum electrode) 8, in this order, on the glass substrate 1 on which an ITO electrode had been previously formed as a transparent anode 2.

Specifically, the glass substrate 1 on which ITO having a film thickness of 150 nm had been formed was washed with an organic solvent, and its surface was then subjected to washing by an oxygen plasma treatment. Thereafter, the ITO electrode-attached glass substrate was fixed in a vacuum vapor depositor, and the pressure therein was reduced to 0.001 Pa or less. NPD was formed as the hole-transport layer 3 at a vapor deposition rate of 6 nm/min in a film thickness of 50 nm so as to cover the transparent anode 2. Alq$_3$ was formed as the luminescent layer 4 on the hole-transport layer 3 at a vapor deposition rate of 6 nm/min in a film thickness of 20 nm. The compound (Compound 11) of Example 1 of the present invention was formed as hole-blocking layer-cum-electron-transport layers 5 and 6 on the luminescent layer 4 at a vapor deposition rate of 6 nm/min in a film thickness of 30 nm. Lithium fluoride was formed as the electron-injection layer 7 on the hole-blocking layer-cum-electron-transport layers 5 and 6 at a vapor deposition rate of 0.6 nm/min in a film thickness of 0.5 nm. Finally, aluminum was formed by vapor deposition in a film thickness of 150 nm to form a cathode 8. Characteristics of the organic EL device thus prepared were measured in the air at an ordinary temperature.

Specifically, luminescent characteristics when passing a current having current density of 10 mA/cm$^2$ through the organic EL device produced by using the compound (Compound 11) of Example 1 of the present invention were measured. The measurement results are shown together in Table 1.

EXAMPLE 6

An organic EL device was produced under the same conditions as in Example 5 except that the compound (Compound 20) of Example 2 of the present invention was formed as a material of the hole-blocking layer-cum-electron-transport layer 5 and 6 in a film thickness of 30 nm, in place of the compound (Compound 11) of Example 1 of the present invention. Characteristics of the organic EL device thus produced were measured in the air at an ordinary temperature.

Specifically, luminescent characteristics when passing a current having current density of 10 mA/cm$^2$ through the organic EL device produced were measured. The measurement results are shown together in Table 1.

COMPARATIVE EXAMPLE 1

For the sake of comparison, an organic EL device was produced under the same conditions as in Example 5 except that the material of the hole-blocking layer-cum-electron-transport layer 5 and 6 was changed to $Alq_3$ which was used as the electron-transport layer 6. Characteristics of the organic EL device thus prepared were measured in the air at an ordinary temperature.

Specifically, luminescent characteristics when passing a current having current density of 10 mA/cm² through the organic EL device produced were measured. The measurement results are shown together in Table 1.

invention was formed as the electron-transport layer 6 on the hole-blocking layer 5 at a vapor deposition rate of 6 nm/min in a film thickness of 30 nm. Lithium fluoride was formed as the electron-injection layer 7 on the electron-transport layer 6 at a vapor deposition rate of 0.6 nm/min in a film thickness of 0.5 nm. Finally, aluminum was formed by vapor deposition in a film thickness of 150 nm to form the cathode 8. Characteristics of the organic EL device thus prepared were measured in the air at an ordinary temperature.

Specifically, luminescent characteristics when passing a current having current density of 10 mA/cm² through the organic EL device produced by using the compound (Com-

TABLE 1

|  |  | Voltage [V] (@10 mA/cm²) | Luminance [cd/m²] (@10 mA/cm²) | Luminous efficiency [cd/A] (@10 mA/cm²) | Power efficiency [lm/W] (@10 mA/cm²) |
| --- | --- | --- | --- | --- | --- |
| Ex. 5 | Compound 11 | 3.44 | 264 | 2.64 | 2.41 |
| Ex. 6 | Compound 20 | 3.73 | 321 | 3.21 | 2.70 |
| Comp. Ex. 1 | Alq₃ | 5.66 | 270 | 2.70 | 1.50 |

As shown in Table 1, the driving voltage when passing the current having current density of 10 mA/cm² through was lowered to as 3.44V in the compound (Compound 11) of Example 1 of the present invention and 3.73V in the compound (Compound 20) of Example 2 of the present invention, as compared with 5.66V in $Alq_3$. Furthermore, the luminance and the luminous efficiency when passing the current having current density of 10 mA/cm² through were nearly equivalent or was improved. The power efficiency was 2.41 lm/W in the compound (Compound 11) of Example 1 of the present invention and 2.70 lm/W in the compound (Compound 20) of Example 2 of the present invention, as compared with 1.50 lm/W in $Alq_3$, and thus was greatly improved.

EXAMPLE 7

The glass substrate 1 on which ITO having a film thickness of 150 nm had been formed was washed with an organic solvent, and its surface was then subjected to washing by an oxygen plasma treatment. Thereafter, the ITO electrode-attached glass substrate was fixed in a vacuum vapor depositor, and the pressure therein was reduced to 0.001 Pa or less. NPD was formed as the hole-transport layer 3 at a vapor deposition rate of 6 nm/min in a film thickness of 30 nm so as to cover the transparent anode 2. CBP and Ir(ppy)₃ were formed as the luminescent layer 4 on the hole-transport layer 3 by binary vacuum deposition (vapor deposition rate: 6 nm/min) in a film thickness of 40 nm while controlling such that the compositional ratio became CBP : Ir(ppy)₃=93:7. BCP was formed as the hole-blocking layer 5 on the luminescent layer 4 at a vapor deposition rate of 6 nm/min in a film thickness of 15 nm. The compound (Compound 11) of Example 1 of the present pound 11) of Example 1 of the present invention were measured. The measurement results are shown together in Table 2.

EXAMPLE 8

An organic EL device was produced under the same conditions as in Example 7 except that the compound (Compound 20) of Example 2 of the present invention was formed as a material of the electron-transport layer 6 in a film thickness of 30 nm, in place of the compound (Compound 11) of Example 1 of the present invention. Characteristics of the organic EL device thus prepared were measured in the air at an ordinary temperature.

Specifically, luminescent characteristics when passing current having current density of 10 mA/cm² through the organic EL device produced were measured. The measurement results are shown together in Table 2.

COMPARATIVE EXAMPLE 2

For the sake of comparison, an organic EL device was produced under the same conditions as in Example 7 except that the material of the electron-transport layer 6 was changed to $Alq_3$. Characteristics of the organic EL device thus prepared were measured in the air at an ordinary temperature.

Specifically, luminescent characteristics when passing a current having current density of 10 mA/cm² through the organic EL device produced were measured. The measurement results are shown together in Table 2.

TABLE 2

|  |  | Voltage [V] (@10 mA/cm²) | Luminance [cd/m²] (@10 mA/cm²) | Luminous efficiency [cd/A] (@10 mA/cm²) | Power efficiency [lm/W] (@10 mA/cm²) |
| --- | --- | --- | --- | --- | --- |
| Ex. 7 | Compound 11 | 9.22 | 2711 | 27.11 | 9.24 |
| Ex. 8 | Compound 20 | 6.15 | 2525 | 25.25 | 13.10 |
| Comp. Ex. 2 | Alq₃ | 11.04 | 2826 | 28.26 | 8.04 |

As shown in Table 2, the driving voltage when passing the current having current density of 10 mA/cm² through was lowered as 9.22V in the compound (Compound 11) of Example 1 of the present invention and 6.15V in the compound (Compound 20) of Example 2 of the present invention, as compared with 11.04V in Alq₃. Furthermore, the luminance and the luminous efficiency when passing the current having current density of 10 mA/cm² through showed nearly equivalent values. The power efficiency was 9.24 lm/W in the compound (Compound 11) of Example 1 of the present invention and 13.10 lm/W in the compound (Compound 20) of Example 2 of the present invention, as compared with 8.04 lm/W in Alq₃, and thus was greatly improved.

As is apparent from those results, it was found that the organic EL device using a compound having a benzotriazole ring structure and a pyridine ring structure of the present invention can achieve great improvement in power efficiency and remarkable decrease in practical driving voltage, as compared with the device using Alq₃ used as the general electron-transport material. Furthermore, from the fact that the organic EL device using a compound having a benzotriazole ring structure and a pyridine ring structure of the present invention has the luminous efficiency (cd/A) per unit current (mA/cm²) equivalent to that of the device using Alq₃ used as the general electron-transport material, it can be found that great improvement in the luminous efficiency (cd/W) per unit electrical energy (W) can be achieved.

It is predicted from the remarkable decrease of driving voltage in the organic EL device using the compound having a benzotriazole ring structure and a pyridine ring structure of the present invention, that the electron moving rate of the compound having a benzotriazole ring structure and a pyridine ring structure of the present invention is much faster that of Alq₃ which is the general electron-transport material.

While the present invention has been described in detail and by reference to the specific embodiments, it is apparent to one skilled in the art that various modifications or changes can be made without departing the spirit and scope of the present invention.

The present application is based on Japanese Patent Application No. 2009-065467 filed on Mar. 18, 2009, the contents of which are incorporated herein by reference.

INDUSTRIAL APPLICABILITY

The compound having a benzotriazole ring structure and a pyridine ring structure of the present invention exhibits good electron-injection property and excellent hole-blocking property, and is stable in a thin film state, and is therefore suitable as a compound for an organic EL device. By producing an organic EL device using the compound, high luminous efficiency and power efficiency can be obtained, and in addition to this, practical driving voltage can be decreased and durability can be improved. It becomes possible to spread onto utilization for, for example, home electric appliances and lighting.

DESCRIPTION OF REFERENCE NUMERALS AND SIGNS

1 Glass substrate
2 Transparent anode
3 Hole-transport layer
4 Luminescent layer
5 Hole-blocking layer
6 Electron-transport layer
7 Electron-injection layer
8 Cathode

The invention claimed is:

1. A compound having a benzotriazole ring structure represented by formula (1):

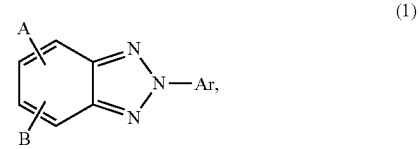

wherein

Ar represents a substituted or unsubstituted aromatic hydrocarbon group, a substituted or unsubstituted aromatic heterocyclic group, or a substituted or unsubstituted condensed polycyclic aromatic group; and A and B are the same as or different from each other and each represent a hydrogen atom or a monovalent group of formula (2) provided that A and B are not simultaneously hydrogen atoms:

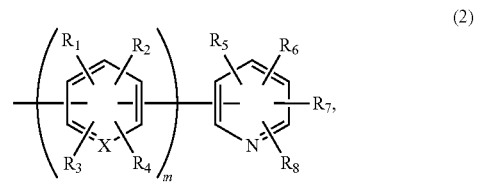

wherein $R_1$ to $R_8$ are the same as or different from each other and each represent a hydrogen atom, a deuterium atom, a fluorine atom, a chlorine atom, a cyano group, a trifluoromethyl group, a linear alkyl group having 1 to 6 carbon atoms, a branched alkyl group having 3 to 6 carbon atoms, a substituted or unsubstituted aromatic hydrocarbon group, a substituted or unsubstituted aromatic heterocyclic group, or a substituted or unsubstituted condensed polycyclic aromatic group;

m is an integer of 1 or 2,

X represents a carbon atom or a nitrogen atom, wherein when X is a nitrogen atom, the nitrogen atom does not have substituents or bonding groups of $R_1$, $R_2$, and $R_3$, and there is no $R_4$; and wherein when m is 2, a plurality of $R_1$, $R_2$, $R_3$, $R_4$, and X each are the same or different.

2. The compound of claim 1, wherein m is 1 in formula (2).

3. The compound of claim 1, wherein m is 1 and X is a nitrogen atom in formula (2).

4. The compound of claim 1, wherein m is 2 in formula (2).

5. The compound of claim 1, wherein m is 2 and all X's are nitrogen atoms in formula (2).

6. An organic electroluminescence device, comprising:

a pair of electrodes; and at least one organic layer sandwiched therebetween, wherein the device comprises a compound having a benzotriazole ring structure represented by formula (1), as a constituent material of at least one organic layer:

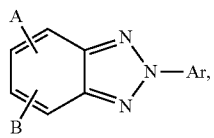

(1)

wherein

Ar represents a substituted or unsubstituted aromatic hydrocarbon group, a substituted or unsubstituted aromatic heterocyclic group, or a substituted or unsubstituted condensed polycyclic aromatic group;

A and B are the same as or different from each other and each represent a hydrogen atom or a monovalent group of formula (2), provided that A and B are not simultaneously hydrogen atoms:

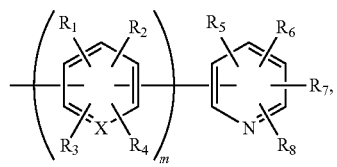

(2)

wherein $R_1$ to $R_8$ are the same as or different from each other and each represent a hydrogen atom, a deuterium atom, a fluorine atom, a chlorine atom, a cyano group, a trifluoromethyl group, a linear alkyl group having 1 to 6 carbon atoms, a branched alkyl group having 3 to 6 carbon atoms, a substituted or unsubstituted aromatic hydrocarbon group, a substituted or unsubstituted aromatic heterocyclic group, or a substituted or unsubstituted condensed polycyclic aromatic group, m is an integer of 1 or 2, X represents a carbon atom or a nitrogen atom, wherein when X is a nitrogen atom, the nitrogen atom does not have substituents or bonding groups of $R_1$, $R_2$, and $R_3$, and there is no $R_4$; and wherein when m is 2, a plurality of $R_1$, $R_2$, $R_3$, and $R_4$, and X each are the same or different.

7. The device of claim 6, wherein the organic layer is an electron-transport layer, and the compound of formula (1) is at least one constituent material in the electron-transport layer.

8. The device of claim 6, wherein the organic layer is a hole-blocking layer, and the compound of formula (1) is at least one constituent material in the hole-blocking layer.

9. The device of claim 6, wherein the organic layer is a luminescent layer, and the compound of formula (1) is at least one constituent material in the luminescent layer.

10. The device of claim 6, wherein the organic layer is an electron-injection layer, and the compound of formula (1) is at least one constituent material in the electron-injection layer.

11. The compound of claim 1, wherein both A and B are a monovalent group of formula (2), and in the monovalent group of at least one of A and B, m is 1.

12. The compound of claim 1, wherein both A and B are a monovalent group of formula (2), and in the monovalent group of at least one of A and B, m is 1 and X is a nitrogen atom.

13. The compound of claim 1, wherein both A and B are a monovalent group of formula (2), and in the monovalent group of at least one of A and B, m is 2.

14. The compound of claim 4, wherein both A and B are a monovalent group of formula (2), and in the monovalent group of at least one of A and B, X's are nitrogen atoms.

15. The compound of claim 1, wherein both A and B are the monovalent group of formula (2), and wherein m is 1.

* * * * *